(12) United States Patent
Hsu

(10) Patent No.: US 7,256,015 B2
(45) Date of Patent: Aug. 14, 2007

(54) TALL-1 RECEPTOR MOLECULES AND USES THEREOF

(75) Inventor: Hailing Hsu, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 115 days.

(21) Appl. No.: 10/251,947

(22) Filed: Sep. 20, 2002

(65) Prior Publication Data

US 2003/0099990 A1 May 29, 2003

Related U.S. Application Data

(60) Provisional application No. 60/324,238, filed on Sep. 21, 2001.

(51) Int. Cl.
*C12N 15/12* (2006.01)
*C12N 15/62* (2006.01)

(52) U.S. Cl. .................. 435/69.1; 435/69.7; 435/252.3; 435/320.1; 536/23.4; 536/23.5

(58) Field of Classification Search ............... 435/69.1, 435/69.7, 252.3, 320.1; 530/350; 536/23.4–23.5
See application file for complete search history.

(56) References Cited

U.S. PATENT DOCUMENTS

2003/0092164 A1  5/2003  Gross et al.
2003/0103986 A1  6/2003  Rixon et al.

FOREIGN PATENT DOCUMENTS

WO   WO 01/60397 A1   11/2000

OTHER PUBLICATIONS

Park et al. Systematic Mutational Analysis of the Death Domain of the Tumor Necrosis Factor Receptor 1-associated Protein TRADD. Apr. 19, 1996, Journal of Biological Chemistry, vol. 271, No. 16, pp. 9858-9862.*
Thompson et al., "BAFF-R, a Newly Identified TNF Receptor That Specifically Interacts with BAFF," *Science*, 293:2108-11 (Sep. 14, 2001).
Xia et al., "TACI Is a TRAF-interacting Receptor for TALL-1, a Tumor Necrosis Factor Family Member Involved in B Cell Regulation," *J. Exp. Med.*, 192:137-43 (Jul. 3, 2000).
Yu et al., APRIL and TALL-1 and receptors BCMA and TACI: system for regulating humoral immunity, *Nature Immunology*, 1:252-256 (Sep. 2000).
Lacey et al., Osteoprotegerin Ligand Is a Cytokine that Regulates Osteoclast Differentiation and Activation, *Cell*, 93:165-76 (Apr. 17, 1988).
Chicheportiche et al., TWEAK, a New Secreted Ligand in the Tumor Necrosis Factor Family That Weakly Induces Apoptosis, *The Journal of Biological Chemistry*, 272:32401-10 (1997).
Mauri et al., "LIGHT, a New Member of the TNF Superfamily, and Lymphotoxin α Are Ligands for Herpesvirus Entry Mediator," *Immunity*, 8:21-30, (Jan. 1988).
Hahne et al., APRIL, a New Ligand of the Tumor Necrosis Factor Family, Stimulates Tumor Cell Growth, *J. Exp. Med.*, 188:1185-90 (Sep. 21, 1998).
Shu et al., "TALL-1 is a novel member of the TNF family that is down-regulated by mitogens," *Journal of Leukocyte Biology*, 65:680-683 (May 1999).
Smith et al., "The TNF Receptor Superfamily of Cellular and Viral Proteins: Activation, Costimulation, and Death," *Cell*, 76:959-962 (Mar. 25, 1994).
Tracey et al., "Tumor Necrosis Factor: A Pleiotropic Cytokine and Therapuetic Target," *Annu. Rev. Med.* 45:491-503 (1994).
Banner et al., "Crystal Structure of the Soluble Human 55 kd TNF Receptor-Human TNFβ Complex: Implications for TNF Receptor Activation," *Cell*, 73:431-445 (May 7, 1993).
Nagata et al., Fas and Fas ligand: *lpr* and *gld* mutations, *Immunology Today*, 16:39-43 (1995).
Castro et al., "Fas Modulation of Apoptosis during Negative Selection of Thymocytes," *Immunity*, 5:617-27 (Dec. 1996).
Noelle et al., "CD40 and Its Ligand in Host Defense," *Immunity*, 4:415-419 (May 1996).
Wallach et al., "Tumor Necrosis Factor Receptor and Fas Signaling Mechanisms," *Annu. Rev. Immunol.*, 17:331-67 (1999).
Hsu et al., "Tumor necrosis factor receptor family member RANK mediates osteoclast differentiation and activation induced by osteoprotegerin ligand," *Proc. Natl. Acad. Sci.* 96:3540-45 (Mar. 1999).

* cited by examiner

*Primary Examiner*—John Ulm
(74) *Attorney, Agent, or Firm*—McDonnell Boehnen Hulbert & Berghoff LLP

(57) ABSTRACT

The present invention provides tumor necrosis factor and apoptosis ligand-related leukocyte-expressed ligand 1 receptor (TALL-1R) polypeptides and nucleic acid molecules encoding the same. The invention also provides selective binding agents, vectors, host cells, and methods for producing TALL-1R polypeptides. The invention further provides pharmaceutical compositions and methods for the diagnosis, treatment, amelioration, and/or prevention of diseases, disorders, and conditions associated with TALL-1R polypeptides.

20 Claims, 13 Drawing Sheets

TALL-1 anti-TACI anti-BCMA

FIG. 5

```
gcgtccggcg gcagcgctgg cacc atg agg cga ggg ccc cgg agc ctg cga      51
                            Met Arg Arg Gly Pro Arg Ser Leu Arg
                             1               5 ggc agg gac gcg ccg gtc ccc acg ccc tgc gtc ccg acc gag tgc tac     99
Gly Arg Asp Ala Pro Val Pro Thr Pro Cys Val Pro Thr Glu Cys Tyr
 10              15                  20                  25 gac ctg ctg gtc cgt aaa tgc gtg gac tgt agg ctc cta cgc aaa tcg    147
Asp Leu Leu Val Arg Lys Cys Val Asp Cys Arg Leu Leu Arg Lys Ser
             30                  35                  40 ccg ccg aaa aca gca gct gga gcc agc agc cct gca ccc ggg acg gcg    195
Pro Pro Lys Thr Ala Ala Gly Ala Ser Ser Pro Ala Pro Gly Thr Ala
         45                  50                  55 ctg cag ccg cag gag tcg gtg ggc acg ggg tcc ggc gag gtg tcg ctg    243
Leu Gln Pro Gln Glu Ser Val Gly Thr Gly Ser Gly Glu Val Ser Leu
         60                  65                  70 ccc ctt ccc ggg ctg ctc ttt ggc gcc ccg gcg ctc ctc ggc ctg gta    291
Pro Leu Pro Gly Leu Leu Phe Gly Ala Pro Ala Leu Leu Gly Leu Val
     75                  80                  85 ctg gtc ctg gcg ctg gtc ctg gtg ggc ctg gtg agc tgg agg cgg cga    339
Leu Val Leu Ala Leu Val Leu Val Gly Leu Val Ser Trp Arg Arg Arg
 90                  95                 100                 105 cag cag cgg ctt cgc ggg gca gcc tcg act gag gcc ccc gac gga gac    387
Gln Gln Arg Leu Arg Gly Ala Ala Ser Thr Glu Ala Pro Asp Gly Asp
                 110                 115                 120 aag gcc gca gcc cca gag ccc ctg gac aag gtc atc att ttg tct cca    435
Lys Ala Ala Ala Pro Glu Pro Leu Asp Lys Val Ile Ile Leu Ser Pro
                 125                 130                 135 gga acc act gat gcc aca gct cct gcc tgg ccc cct cct gga gaa gac    483
Gly Thr Thr Asp Ala Thr Ala Pro Ala Trp Pro Pro Pro Gly Glu Asp
         140                 145                 150 caa gga acc acc cca cct ggc cac agc atc cct gtg cca gcc aca gag    531
Gln Gly Thr Thr Pro Pro Gly His Ser Ile Pro Val Pro Ala Thr Glu
     155                 160                 165 ctg ggc tcc act gaa ctg gtg acc acc aag aca gct ggc cct gag caa    579
Leu Gly Ser Thr Glu Leu Val Thr Thr Lys Thr Ala Gly Pro Glu Gln
170                 175                 180                 185 taatagcaga gagctggcag gaggtgcctc ctggccttcc tcccgacccc cagccagggg  639
cttggaaatc aaattcagct c                                            660
```

FIG. 6

```
ctcgtgcggc agcgctggca cc atg agg cga ggg ccc cgg agc ctg cga ggc      52
                          Met Arg Arg Gly Pro Arg Ser Leu Arg Gly
                           1               5                  10 agg gac gcg ccg gtc ccc acg ccc tgc gtc ccg acc gag tgc tac gac      100
Arg Asp Ala Pro Val Pro Thr Pro Cys Val Pro Thr Glu Cys Tyr Asp
                15                  20                  25 ctg ctg gtc cgt aaa tgc gtg gac tgt agg ctc cta cgc aaa tcg ccg      148
Leu Leu Val Arg Lys Cys Val Asp Cys Arg Leu Leu Arg Lys Ser Pro
                30                  35                  40 ccg aaa aca gca gct gga gcc agc agc cct gca ccc ggg acg gcg ctg      196
Pro Lys Thr Ala Ala Gly Ala Ser Ser Pro Ala Pro Gly Thr Ala Leu
                45                  50                  55 cag ccg cag gag tcg gtg ggc acg ggg tcc ggc gag gtg tcg ctg ccc      244
Gln Pro Gln Glu Ser Val Gly Thr Gly Ser Gly Glu Val Ser Leu Pro
        60                  65                  70 ctt ccc ggg ctg ctc ttt ggc gcc ccg gcg ctc ctc ggc ctg gta ctg      292
Leu Pro Gly Leu Leu Phe Gly Ala Pro Ala Leu Leu Gly Leu Val Leu
 75                  80                  85                  90 gtc ctg gcg ctg gtc ctg gtg ggc ctg gtg agc tgg agg cgg cga cag      340
Val Leu Ala Leu Val Leu Val Gly Leu Val Ser Trp Arg Arg Arg Gln
                95                 100                 105 cag cgg ctt cgc ggg gca gcc tcg act gag gcc ccc gac gga gac aag      388
Gln Arg Leu Arg Gly Ala Ala Ser Thr Glu Ala Pro Asp Gly Asp Lys
                110                 115                 120 gcc gga acc act gat gcc aca gct cct gcc tgg ccc cct cct gga gaa      436
Ala Gly Thr Thr Asp Ala Thr Ala Pro Ala Trp Pro Pro Pro Gly Glu
                125                 130                 135 gac caa gga acc acc cca cct ggc cac agc atc cct gtg cca gcc aca      484
Asp Gln Gly Thr Thr Pro Pro Gly His Ser Ile Pro Val Pro Ala Thr
                140                 145                 150 gag ctg ggc tcc act gaa ctg gtg acc acc aag aca gct ggc cct gag      532
Glu Leu Gly Ser Thr Glu Leu Val Thr Thr Lys Thr Ala Gly Pro Glu
155                 160                 165                 170 caa taatagcaga gagctggcag gaagtgcctc ctggccttcc taccgacccc           585
Gln aaccaggggc ttgga                                                      600
```

FIG. 7

```
gcgtccgtgc ggcagcgctg gcacc atg agg cga ggg ccc cgg agc ctg cga    52
                              Met Arg Arg Gly Pro Arg Ser Leu Arg
                              1                 5 ggc agg gac gcg ccg gtc ccc acg ccc tgc gtc ccg acc gag tgc tac   100
Gly Arg Asp Ala Pro Val Pro Thr Pro Cys Val Pro Thr Glu Cys Tyr
10              15                  20                  25 gac ctg ctg gtc cgt aaa tgc gtg gac tgt agg ctc cta cgc aaa tcg   148
Asp Leu Leu Val Arg Lys Cys Val Asp Cys Arg Leu Leu Arg Lys Ser
                30                  35                  40 ccg ccg aaa aca gct gga gcc agc agc cct gca ccc ggg acg gcg ctg   196
Pro Pro Lys Thr Ala Gly Ala Ser Ser Pro Ala Pro Gly Thr Ala Leu
            45                  50                  55 cag ccg cag gag tcg gtg ggc acg ggg tcc ggc gag gtg tcg ctg ccc   244
Gln Pro Gln Glu Ser Val Gly Thr Gly Ser Gly Glu Val Ser Leu Pro
        60                  65                  70 ctt ccc ggg ctg ctc ttt ggc gcc ccg gcg ctc ctc ggc ctg gta ctg   292
Leu Pro Gly Leu Leu Phe Gly Ala Pro Ala Leu Leu Gly Leu Val Leu
    75                  80                  85 gtc ctg gcg ctg gtc ctg gtg ggc ctg gtg agc tgg agg cgg cga cag   340
Val Leu Ala Leu Val Leu Val Gly Leu Val Ser Trp Arg Arg Arg Gln
90                  95                  100                 105 cag cgg ctt cgc ggg gca gcc tcg act gag gcc ccc gac gga gac aag   388
Gln Arg Leu Arg Gly Ala Ala Ser Thr Glu Ala Pro Asp Gly Asp Lys
                110                 115                 120 gcc gga acc act gat gcc aca gct cct gcc tgg ccc cct cct gga gaa   436
Ala Gly Thr Thr Asp Ala Thr Ala Pro Ala Trp Pro Pro Pro Gly Glu
            125                 130                 135 gac caa gga acc acc cca cct ggc cac agc atc cct gtg cca gcc aca   484
Asp Gln Gly Thr Thr Pro Pro Gly His Ser Ile Pro Val Pro Ala Thr
        140                 145                 150 gag ctg ggc tcc act gaa ctg gtg acc acc aag aca gct ggc cct gag   532
Glu Leu Gly Ser Thr Glu Leu Val Thr Thr Lys Thr Ala Gly Pro Glu
    155                 160                 165 caa taatagcaga gagctggcag gaggtgcctc ctggccttcc tcccgacccc        585
Gln
170 cagccagggg cttgg                                                   600
```

FIG. 8A

```
711   MRRGPRSLRG  RDAPVPTPCV  PTECYDLLVR  KCVDCRLLRK  SPPKTAAGAS
713   MRRGPRSLRG  RDAPVPTPCV  PTECYDLLVR  KCVDCRLLRK  SPPKTAAGAS
706   MRRGPRSLRG  RDAPVPTPCV  PTECYDLLVR  KCVDCRLLRK  SPPKT AGAS
710   MRRGPRSLRG  RDAPVPTPCV  PTECYDLLVR  KCVDCRLLRK  SPPKTAAGAS

711   SPAPGTALQP  QESVGTGSGE  VSLPLPGLLF  GAPALLGLVL  VLALVLVGLV
713   SPAPGTALQP  QESVGTGSGE  VSLPLPGLLF  GAPALLGLVL  VLALVLVGLV
706   SPAPGTALQP  QESVGTGSGE  VSLPLPGLLF  GAPALLGLVL  VLALVLVGLV
710   SPAPGTALQP  QESVGTGSGE  VSLPLPGLLF  GAPALLGLVL  VLALVLVGLV

711   SWRRRQQRLR  GAASTEAPDG  DKA.......  .......GTT  DATAPAWPPP
713   SWRRRQQRLR  GAASTEAPDG  DKA.......  .......GTT  DATAPAWPPP
706   SWRRRQQRLR  GAASTEAPDG  DKA.......  .......GTT  DATAPAWPPP
710   SWRRRQQRLR  GAASTEAPDG  DKAAAPEPLD  KVIILSPGTT  DATAPAWPPP

711   GEDQGTTPPG  HSIPVPATEL  GSTELVTTKT  AGPEQ
713   GEDQGTTPPG  HSIPVPATEL  GSTELVTTKT  AGPEQ
706   GEDQGTTPPG  HSIPVPATEL  GSTELVTTKT  AGPEQ
710   GEDQGTTPPG  HSIPVPATEL  GSTELVTTKT  AGPEQ
```

FIG. 8B

Met Arg Arg Gly Pro Arg Ser Leu Arg Gly Arg Asp Ala Pro Val Pro
1              5                    10                   15

Thr Pro Cys Val Pro Thr Glu Cys Tyr Asp Leu Leu Val Arg Lys Cys
              20                   25                   30

Val Asp Cys Arg Leu Leu Arg Lys Ser Pro Pro Lys Thr Xaa Ala Gly
              35                   40                   45

Ala Ser Ser Pro Ala Pro Gly Thr Ala Leu Gln Pro Gln Glu Ser Val
    50                   55                   60

Gly Thr Gly Ser Gly Glu Val Ser Leu Pro Leu Pro Gly Leu Leu Phe
65                   70                   75                   80

Gly Ala Pro Ala Leu Leu Gly Leu Val Leu Val Leu Ala Leu Val Leu
              85                   90                   95

Val Gly Leu Val Ser Trp Arg Arg Arg Gln Gln Arg Leu Arg Gly Ala
              100                  105                  110

Ala Ser Thr Glu Ala Pro Asp Gly Asp Lys Ala Xaa Xaa Xaa Xaa Xaa
         115                  120                  125

Xaa Xaa Xaa Xaa Xaa Xaa Xaa Xaa Xaa Xaa Gly Thr Thr Asp Ala Thr
         130                  135                  140

Ala Pro Ala Trp Pro Pro Pro Gly Glu Asp Gln Gly Thr Thr Pro Pro
145                  150                  155                  160

Gly His Ser Ile Pro Val Pro Ala Thr Glu Leu Gly Ser Thr Glu Leu
              165                  170                  175

Val Thr Thr Lys Thr Ala Gly Pro Glu Gln
              180                  185

SEQUENCE LISTING

<160> NUMBER OF SEQ ID NOS: 14

<210> SEQ ID NO 1
<211> LENGTH: 660
<212> TYPE: DNA
<213> ORGANISM: Homo sapiens
<220> FEATURE:
<221> NAME/KEY: CDS
<222> LOCATION: (25)..(579)

<400> SEQUENCE: 1
gcgtccggcg gcagcgctgg cacc atg agg cga ggg ccc cgg agc ctg cga    51

```
                Met Arg Arg Gly Pro Arg Ser Leu Arg
                  1               5 ggc agg gac gcg ccg gtc ccc acg ccc tgc gtc ccg acc gag tgc tac        99
Gly Arg Asp Ala Pro Val Pro Thr Pro Cys Val Pro Thr Glu Cys Tyr
 10              15                  20                  25 gac ctg ctg gtc cgt aaa tgc gtg gac tgt agg ctc cta cgc aaa tcg       147
Asp Leu Leu Val Arg Lys Cys Val Asp Cys Arg Leu Leu Arg Lys Ser
                 30                  35                  40 ccg ccg aaa aca gca gct gga gcc agc agc cct gca ccc ggg acg gcg       195
Pro Pro Lys Thr Ala Ala Gly Ala Ser Ser Pro Ala Pro Gly Thr Ala
                 45                  50                  55 ctg cag ccg cag gag tcg gtg ggc acg ggg tcc ggc gag gtg tcg ctg       243
Leu Gln Pro Gln Glu Ser Val Gly Thr Gly Ser Gly Glu Val Ser Leu
             60                  65                  70 ccc ctt ccc ggg ctg ctc ttt ggc gcc ccg gcg ctc ctc ggc ctg gta       291
Pro Leu Pro Gly Leu Leu Phe Gly Ala Pro Ala Leu Leu Gly Leu Val
         75                  80                  85 ctg gtc ctg gcg ctg gtc ctg gtg ggc ctg gtg agc tgg agg cgg cga       339
Leu Val Leu Ala Leu Val Leu Val Gly Leu Val Ser Trp Arg Arg Arg
 90                  95                 100                 105 cag cag cgg ctt cgc ggg gca gcc tcg act gag gcc ccc gac gga gac       387
Gln Gln Arg Leu Arg Gly Ala Ala Ser Thr Glu Ala Pro Asp Gly Asp
                110                 115                 120 aag gcc gca gcc cca gag ccc ctg gac aag gtc atc att ttg tct cca       435
Lys Ala Ala Ala Pro Glu Pro Leu Asp Lys Val Ile Ile Leu Ser Pro
                125                 130                 135 gga acc act gat gcc aca gct cct gcc tgg ccc cct cct gga gaa gac       483
Gly Thr Thr Asp Ala Thr Ala Pro Ala Trp Pro Pro Pro Gly Glu Asp
                140                 145                 150 caa gga acc acc cca cct ggc cac agc atc cct gtg cca gcc aca gag       531
Gln Gly Thr Thr Pro Pro Gly His Ser Ile Pro Val Pro Ala Thr Glu
    155                 160                 165 ctg ggc tcc act gaa ctg gtg acc acc aag aca gct ggc cct gag caa       579
Leu Gly Ser Thr Glu Leu Val Thr Thr Lys Thr Ala Gly Pro Glu Gln
170                 175                 180                 185 taatagcaga gagctggcag gaggtgcctc ctggccttcc tcccgacccc cagccagggg    639
cttggaaatc aaattcagct c                                              660

<210> SEQ ID NO 2
<211> LENGTH: 185
<212> TYPE: PRT
<213> ORGANISM: Homo sapiens

<400> SEQUENCE: 2

Met Arg Arg Gly Pro Arg Ser Leu Arg Gly Arg Asp Ala Pro Val Pro
  1               5                  10                  15

Thr Pro Cys Val Pro Thr Glu Cys Tyr Asp Leu Leu Val Arg Lys Cys
                 20                  25                  30

Val Asp Cys Arg Leu Leu Arg Lys Ser Pro Pro Lys Thr Ala Ala Gly
             35                  40                  45

Ala Ser Ser Pro Ala Pro Gly Thr Ala Leu Gln Pro Gln Glu Ser Val
         50                  55                  60

Gly Thr Gly Ser Gly Glu Val Ser Leu Pro Leu Pro Gly Leu Leu Phe
 65                  70                  75                  80

Gly Ala Pro Ala Leu Leu Gly Leu Val Leu Val Leu Ala Leu Val Leu
                 85                  90                  95

Val Gly Leu Val Ser Trp Arg Arg Arg Gln Gln Arg Leu Arg Gly Ala
                100                 105                 110
```

```
Ala Ser Thr Glu Ala Pro Asp Gly Asp Lys Ala Ala Pro Glu Pro
        115                 120                 125

Leu Asp Lys Val Ile Ile Leu Ser Pro Gly Thr Thr Asp Ala Thr Ala
    130                 135                 140

Pro Ala Trp Pro Pro Gly Glu Asp Gln Gly Thr Thr Pro Pro Gly
145             150                 155                 160

His Ser Ile Pro Val Pro Ala Thr Glu Leu Gly Ser Thr Glu Leu Val
                165                 170                 175

Thr Thr Lys Thr Ala Gly Pro Glu Gln
            180                 185

<210> SEQ ID NO 3
<211> LENGTH: 600
<212> TYPE: DNA
<213> ORGANISM: Homo sapiens
<220> FEATURE:
<221> NAME/KEY: CDS
<222> LOCATION: (23)..(535)

<400> SEQUENCE: 3
ctcgtgcggc agcgctggca cc atg agg cga ggg ccc cgg agc ctg cga ggc      52
                         Met Arg Arg Gly Pro Arg Ser Leu Arg Gly
                           1               5                  10 agg gac gcg ccg gtc ccc acg ccc tgc gtc ccg acc gag tgc tac gac     100
Arg Asp Ala Pro Val Pro Thr Pro Cys Val Pro Thr Glu Cys Tyr Asp
             15                  20                  25 ctg ctg gtc cgt aaa tgc gtg gac tgt agg ctc cta cgc aaa tcg ccg     148
Leu Leu Val Arg Lys Cys Val Asp Cys Arg Leu Leu Arg Lys Ser Pro
         30                  35                  40 ccg aaa aca gca gct gga gcc agc agc cct gca ccc ggg acg gcg ctg     196
Pro Lys Thr Ala Ala Gly Ala Ser Ser Pro Ala Pro Gly Thr Ala Leu
     45                  50                  55 cag ccg cag gag tcg gtg ggc acg ggg tcc ggc gag gtg tcg ctg ccc     244
Gln Pro Gln Glu Ser Val Gly Thr Gly Ser Gly Glu Val Ser Leu Pro
 60                  65                  70 ctt ccc ggg ctg ctc ttt ggc gcc ccg gcg ctc ctc ggc ctg gta ctg     292
Leu Pro Gly Leu Leu Phe Gly Ala Pro Ala Leu Leu Gly Leu Val Leu
 75                  80                  85                  90 gtc ctg gcg ctg gtc ctg gtg ggc ctg gtg agc tgg agg cgg cga cag     340
Val Leu Ala Leu Val Leu Val Gly Leu Val Ser Trp Arg Arg Arg Gln
                 95                 100                 105 cag cgg ctt cgc ggg gca gcc tcg act gag gcc ccc gac gga gac aag     388
Gln Arg Leu Arg Gly Ala Ala Ser Thr Glu Ala Pro Asp Gly Asp Lys
            110                 115                 120 gcc gga acc act gat gcc aca gct cct gcc tgg ccc cct cct gga gaa     436
Ala Gly Thr Thr Asp Ala Thr Ala Pro Ala Trp Pro Pro Pro Gly Glu
        125                 130                 135 gac caa gga acc acc cca cct ggc cac agc atc cct gtg cca gcc aca     484
Asp Gln Gly Thr Thr Pro Pro Gly His Ser Ile Pro Val Pro Ala Thr
    140                 145                 150 gag ctg ggc tcc act gaa ctg gtg acc acc aag aca gct ggc cct gag     532
Glu Leu Gly Ser Thr Glu Leu Val Thr Thr Lys Thr Ala Gly Pro Glu
155                 160                 165                 170 caa taatagcaga gagctggcag gaagtgcctc ctggccttcc taccgacccc         585
Gln aaccaggggc ttgga                                                   600

<210> SEQ ID NO 4
<211> LENGTH: 171
```

```
<212> TYPE: PRT
<213> ORGANISM: Homo sapiens

<400> SEQUENCE: 4

Met Arg Arg Gly Pro Arg Ser Leu Arg Gly Arg Asp Ala Pro Val Pro
  1               5                  10                  15

Thr Pro Cys Val Pro Thr Glu Cys Tyr Asp Leu Leu Val Arg Lys Cys
                 20                  25                  30

Val Asp Cys Arg Leu Leu Arg Lys Ser Pro Pro Lys Thr Ala Ala Gly
             35                  40                  45

Ala Ser Ser Pro Ala Pro Gly Thr Ala Leu Gln Pro Gln Glu Ser Val
         50                  55                  60

Gly Thr Gly Ser Gly Glu Val Ser Leu Pro Leu Pro Gly Leu Leu Phe
 65                  70                  75                  80

Gly Ala Pro Ala Leu Leu Gly Leu Val Leu Val Leu Ala Leu Val Leu
                 85                  90                  95

Val Gly Leu Val Ser Trp Arg Arg Gln Gln Arg Leu Arg Gly Ala
                100                 105                 110

Ala Ser Thr Glu Ala Pro Asp Gly Asp Lys Ala Gly Thr Thr Asp Ala
            115                 120                 125

Thr Ala Pro Ala Trp Pro Pro Gly Glu Asp Gln Gly Thr Thr Pro
        130                 135                 140

Pro Gly His Ser Ile Pro Val Pro Ala Thr Glu Leu Gly Ser Thr Glu
145                 150                 155                 160

Leu Val Thr Thr Lys Thr Ala Gly Pro Glu Gln
                165                 170

<210> SEQ ID NO 5
<211> LENGTH: 600
<212> TYPE: DNA
<213> ORGANISM: Homo sapiens
<220> FEATURE:
<221> NAME/KEY: CDS
<222> LOCATION: (26)..(535)

<400> SEQUENCE: 5
gcgtccgtgc ggcagcgctg gcacc atg agg cga ggg ccc cgg agc ctg cga        52
                            Met Arg Arg Gly Pro Arg Ser Leu Arg
                              1               5 ggc agg gac gcg ccg gtc ccc acg ccc tgc gtc ccg acc gag tgc tac       100
Gly Arg Asp Ala Pro Val Pro Thr Pro Cys Val Pro Thr Glu Cys Tyr
 10                  15                  20                  25 gac ctg ctg gtc cgt aaa tgc gtg gac tgt agg ctc cta cgc aaa tcg       148
Asp Leu Leu Val Arg Lys Cys Val Asp Cys Arg Leu Leu Arg Lys Ser
                 30                  35                  40 ccg ccg aaa aca gct gga gcc agc agc cct gca ccc ggg acg gcg ctg       196
Pro Pro Lys Thr Ala Gly Ala Ser Ser Pro Ala Pro Gly Thr Ala Leu
             45                  50                  55 cag ccg cag gag tcg gtg ggc acg ggg tcc ggc gag gtg tcg ctg ccc       244
Gln Pro Gln Glu Ser Val Gly Thr Gly Ser Gly Glu Val Ser Leu Pro
         60                  65                  70 ctt ccc ggg ctg ctc ttt ggc gcc ccg gcg ctc ctc ggc ctg gta ctg       292
Leu Pro Gly Leu Leu Phe Gly Ala Pro Ala Leu Leu Gly Leu Val Leu
     75                  80                  85 gtc ctg gcg ctg gtc ctg gtg ggc ctg gtg agc tgg agg cgg cga cag       340
Val Leu Ala Leu Val Leu Val Gly Leu Val Ser Trp Arg Arg Arg Gln
 90                  95                 100                 105 cag cgg ctt cgc ggg gca gcc tcg act gag gcc ccc gac gga gac aag       388
Gln Arg Leu Arg Gly Ala Ala Ser Thr Glu Ala Pro Asp Gly Asp Lys
```

-continued

```
                110                 115                 120
gcc gga acc act gat gcc aca gct cct gcc tgg ccc cct cct gga gaa    436
Ala Gly Thr Thr Asp Ala Thr Ala Pro Ala Trp Pro Pro Pro Gly Glu
            125                 130                 135 gac caa gga acc acc cca cct ggc cac agc atc cct gtg cca gcc aca    484
Asp Gln Gly Thr Thr Pro Pro Gly His Ser Ile Pro Val Pro Ala Thr
        140                 145                 150 gag ctg ggc tcc act gaa ctg gtg acc acc aag aca gct ggc cct gag    532
Glu Leu Gly Ser Thr Glu Leu Val Thr Thr Lys Thr Ala Gly Pro Glu
    155                 160                 165 caa taatagcaga gagctggcag gaggtgcctc ctggccttcc tcccgacccc        585
Gln
170 cagccagggg cttgg                                                   600

<210> SEQ ID NO 6
<211> LENGTH: 170
<212> TYPE: PRT
<213> ORGANISM: Homo sapiens

<400> SEQUENCE: 6

Met Arg Arg Gly Pro Arg Ser Leu Arg Gly Arg Asp Ala Pro Val Pro
1               5                   10                  15

Thr Pro Cys Val Pro Thr Glu Cys Tyr Asp Leu Leu Val Arg Lys Cys
            20                  25                  30

Val Asp Cys Arg Leu Leu Arg Lys Ser Pro Pro Lys Thr Ala Gly Ala
        35                  40                  45

Ser Ser Pro Ala Pro Gly Thr Ala Leu Gln Pro Gln Glu Ser Val Gly
    50                  55                  60

Thr Gly Ser Gly Glu Val Ser Leu Pro Leu Pro Gly Leu Leu Phe Gly
65                  70                  75                  80

Ala Pro Ala Leu Leu Gly Leu Val Leu Val Leu Ala Leu Val Leu Val
                85                  90                  95

Gly Leu Val Ser Trp Arg Arg Gln Gln Arg Leu Arg Gly Ala Ala
            100                 105                 110

Ser Thr Glu Ala Pro Asp Gly Asp Lys Ala Gly Thr Thr Asp Ala Thr
        115                 120                 125

Ala Pro Ala Trp Pro Pro Gly Glu Asp Gln Gly Thr Thr Pro Pro
    130                 135                 140

Gly His Ser Ile Pro Val Pro Ala Thr Glu Leu Gly Ser Thr Glu Leu
145                 150                 155                 160

Val Thr Thr Lys Thr Ala Gly Pro Glu Gln
                165                 170

<210> SEQ ID NO 7
<211> LENGTH: 171
<212> TYPE: PRT
<213> ORGANISM: Homo sapiens

<400> SEQUENCE: 7

Met Arg Arg Gly Pro Arg Ser Leu Arg Gly Arg Asp Ala Pro Val Pro
1               5                   10                  15

Thr Pro Cys Val Pro Thr Glu Cys Tyr Asp Leu Leu Val Arg Lys Cys
            20                  25                  30

Val Asp Cys Arg Leu Leu Arg Lys Ser Pro Pro Lys Thr Ala Gly
        35                  40                  45

Ala Ser Ser Pro Ala Pro Gly Thr Ala Leu Gln Pro Gln Glu Ser Val
```

-continued

```
                    50                  55                  60
Gly Thr Gly Ser Gly Glu Val Ser Leu Pro Leu Pro Gly Leu Leu Phe
 65                  70                  75                  80

Gly Ala Pro Ala Leu Leu Gly Leu Val Leu Leu Ala Leu Val Leu
                 85                  90                  95

Val Gly Leu Val Ser Trp Arg Arg Gln Gln Arg Leu Arg Gly Ala
                100                 105                 110

Ala Ser Thr Glu Ala Pro Asp Gly Asp Lys Ala Gly Thr Thr Asp Ala
            115                 120                 125

Thr Ala Pro Ala Trp Pro Pro Gly Glu Asp Gln Gly Thr Thr Pro
        130                 135                 140

Pro Gly His Ser Ile Pro Val Pro Ala Thr Glu Leu Gly Ser Thr Glu
145                 150                 155                 160

Leu Val Thr Thr Lys Thr Ala Gly Pro Glu Gln
                165                 170
```

<210> SEQ ID NO 8
<211> LENGTH: 15
<212> TYPE: PRT
<213> ORGANISM: Human immunodeficiency virus type 1

<400> SEQUENCE: 8

```
Gly Gly Gly Gly Tyr Gly Arg Lys Lys Arg Arg Gln Arg Arg Arg
 1               5                  10                  15
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:
      internalizing domain derived from HIV tat protein

<400> SEQUENCE: 9

```
Tyr Gly Arg Lys Lys Arg Arg Gln Arg Arg Arg
 1               5                  10
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: N-terminal
      sequence of TALL-1R::Fc fusion protein encoded by
      pAMG21 TALL-1R::Fc expression construct

<400> SEQUENCE: 10

```
Met Arg Arg Gly Pro Arg Ser
 1               5
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: C-terminal
      sequence of TALL-1R::Fc fusion protein encoded by
      pAMG21 TALL-1R::Fc expression construct

<400> SEQUENCE: 11

```
Ser Leu Ser Pro Gly Lys
 1               5
```

```
<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: fusion
      junction sequence of TALL-1R::Fc fusion protein
      encoded by pAMG21 TALL-1R::Fc expression construct

<400> SEQUENCE: 12

Val Ser Leu Pro Leu Pro Gly Gly Gly Gly Gly Gly Asp Lys Thr His
 1               5                  10                  15
Thr Cys Pro

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: N-terminal
      sequence of purified TALL-1R::Fc fusion protein

<400> SEQUENCE: 13

Ser Leu Arg Gly Arg Asp
 1               5

<210> SEQ ID NO 14
<211> LENGTH: 186
<212> TYPE: PRT
<213> ORGANISM: Artificial Sequence
<220> FEATURE:
<223> OTHER INFORMATION: Description of Artificial Sequence: TALL-1R
      polypeptide derived from the amino acid sequence
      alignment shown in Figure 8A
<220> FEATURE:
<221> NAME/KEY: UNSURE
<222> LOCATION: (46)
<223> OTHER INFORMATION: "Xaa" can be any naturally occurring amino
      acid.
<220> FEATURE:
<221> NAME/KEY: UNSURE
<222> LOCATION: (124)
<223> OTHER INFORMATION: "Xaa" can be any naturally occurring amino
      acid, or is absent.
<220> FEATURE:
<221> NAME/KEY: UNSURE
<222> LOCATION: (125)
<223> OTHER INFORMATION: "Xaa" can be any naturally occurring amino
      acid, or is absent.
<220> FEATURE:
<221> NAME/KEY: UNSURE
<222> LOCATION: (126)
<223> OTHER INFORMATION: "Xaa" can be any naturally occurring amino
      acid, or is absent.
<220> FEATURE:
<221> NAME/KEY: UNSURE
<222> LOCATION: (127)
<223> OTHER INFORMATION: "Xaa" can be any naturally occurring amino
      acid, or is absent.
<220> FEATURE:
<221> NAME/KEY: UNSURE
<222> LOCATION: (128)
<223> OTHER INFORMATION: "Xaa" can be any naturally occurring amino
      acid, or is absent.
<220> FEATURE:
<221> NAME/KEY: UNSURE
<222> LOCATION: (129)
<223> OTHER INFORMATION: "Xaa" can be any naturally occurring amino
      acid, or is absent.
<220> FEATURE:
<221> NAME/KEY: UNSURE
<222> LOCATION: (130)
```

-continued

```
<223> OTHER INFORMATION: "Xaa" can be any naturally occurring amino
      acid, or is absent.
<220> FEATURE:
<221> NAME/KEY: UNSURE
<222> LOCATION: (131)
<223> OTHER INFORMATION: "Xaa" can be any naturally occurring amino
      acid, or is absent.
<220> FEATURE:
<221> NAME/KEY: UNSURE
<222> LOCATION: (132)
<223> OTHER INFORMATION: "Xaa" can be any naturally occurring amino
      acid, or is absent.
<220> FEATURE:
<221> NAME/KEY: UNSURE
<222> LOCATION: (133)
<223> OTHER INFORMATION: "Xaa" can be any naturally occurring amino
      acid, or is absent.
<220> FEATURE:
<221> NAME/KEY: UNSURE
<222> LOCATION: (134)
<223> OTHER INFORMATION: "Xaa" can be any naturally occurring amino
      acid, or is absent.
<220> FEATURE:
<221> NAME/KEY: UNSURE
<222> LOCATION: (135)
<223> OTHER INFORMATION: "Xaa" can be any naturally occurring amino
      acid, or is absent.
<220> FEATURE:
<221> NAME/KEY: UNSURE
<222> LOCATION: (136)
<223> OTHER INFORMATION: "Xaa" can be any naturally occurring amino
      acid, or is absent.
<220> FEATURE:
<221> NAME/KEY: UNSURE
<222> LOCATION: (137)
<223> OTHER INFORMATION: "Xaa" can be any naturally occurring amino
      acid, or is absent.
<220> FEATURE:
<221> NAME/KEY: UNSURE
<222> LOCATION: (138)
<223> OTHER INFORMATION: "Xaa" can be any naturally occurring amino
      acid, or is absent.

<400> SEQUENCE: 14

Met Arg Arg Gly Pro Arg Ser Leu Arg Gly Arg Asp Ala Pro Val Pro
  1               5                  10                  15

Thr Pro Cys Val Pro Thr Glu Cys Tyr Asp Leu Leu Val Arg Lys Cys
             20                  25                  30

Val Asp Cys Arg Leu Leu Arg Lys Ser Pro Pro Lys Thr Xaa Ala Gly
         35                  40                  45

Ala Ser Ser Pro Ala Pro Gly Thr Ala Leu Gln Pro Gln Glu Ser Val
     50                  55                  60

Gly Thr Gly Ser Gly Glu Val Ser Leu Pro Leu Pro Gly Leu Leu Phe
 65                  70                  75                  80

Gly Ala Pro Ala Leu Leu Gly Leu Val Leu Ala Leu Val Leu
                 85                  90                  95

Val Gly Leu Val Ser Trp Arg Arg Gln Gln Arg Leu Arg Gly Ala
             100                 105                 110

Ala Ser Thr Glu Ala Pro Asp Gly Asp Lys Ala Xaa Xaa Xaa Xaa
         115                 120                 125

Xaa Xaa Xaa Xaa Xaa Xaa Xaa Xaa Xaa Gly Thr Thr Asp Ala Thr
     130                 135                 140

Ala Pro Ala Trp Pro Pro Gly Glu Asp Gln Gly Thr Thr Pro Pro
145                 150                 155                 160

Gly His Ser Ile Pro Val Pro Ala Thr Glu Leu Gly Ser Thr Glu Leu
                 165                 170                 175
```

-continued

```
Val Thr Thr Lys Thr Ala Gly Pro Glu Gln
        180                 185
```

TALL-1 RECEPTOR MOLECULES AND USES THEREOF

This application claims the benefit of priority from U.S. Provisional Patent Application No. 60/324,238, filed on Sep. 21, 2001, the disclosure of which is explicitly incorporated by reference herein.

FIELD OF THE INVENTION

The present invention relates to tumor necrosis factor and apoptosis ligand-related leukocyte-expressed ligand 1 receptor (TALL-1R) polypeptides and nucleic acid molecules encoding the same. The invention also relates to selective binding agents, vectors, host cells, and methods for producing TALL-1R polypeptides. The invention further relates to pharmaceutical compositions and methods for the diagnosis, treatment, amelioration, and/or prevention of diseases, disorders, and conditions associated with TALL-1R polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

The isolation of nucleic acid sequences encoding tumor necrosis factors (TNFs) α and β led to the identification of a superfamily of TNF cytokines that includes fas ligand (FasL), CD27 ligand (CD27L), CD30 ligand (CD30L), CD40 ligand (CD40L), TNF-related apoptosis-inducing ligand (TRAIL, also designated as AGP-1), osteoprotegerin binding protein (OPG-BP or OPG ligand), 4-1BB ligand, LIGHT, APRIL, and TALL-1 (also designated as BAFF, THANK, BlyS, and zTNF4). See Smith et al., 1994, *Cell* 76:959-62; Lacey et al., 1998, *Cell* 93:165-76; Chichepotiche et al., 1997, *J. Biol. Chem.* 272:32401-10; Mauri et al., 1998, *Immunity* 8:21-30; Hahne et al., 1998, *J. Exp. Med.* 188:1185-90; Shu et al., 1999, *J. Leukocyte Biology* 65:680-83. The members of this ligand family are unified by their structure, particularly at the C-terminus, and expression in immune compartments (Smith et al., 1994). Furthermore, with the exception of LT-α, all of the members of this family are type II transmembrane proteins, characterized by a conserved 150 amino acid region within the C-terminal extracellular domain, which folds into a characteristic β-pleated sheet sandwich and trimerizes. This conserved region can be proteolyticaly released, thus generating a soluble functional form (Banner et al., 1993, *Cell* 73:431-45).

Many members within this ligand family are expressed in lymphoid enriched tissues and play important roles in the immune system development and modulation (Smith et al., 1994). For example, TNFα, which is mainly synthesized by macrophages, has been shown to be an important mediator for inflammatory responses and immune defenses (Tracey and Cerami, 1994, *Annu. Rev. Med.* 45:491-503). Fas-L, which is predominantly expressed in activated T cells, has been shown to modulate TCR-mediated apoptosis in thymocytes (Nagata and Suda, 1995, *Immunology Today* 16:39-43; Castrim et al., 1996, *Immunity* 5:617-27). CD40L, which is also expressed in activated T cells, provides an essential signal for B cell survival, proliferation, and immunoglobulin isotype switching (Noelle, 1996, *Immunity* 4:415-19).

The cognate receptors for most of the TNF ligand family members have been identified. These receptors share characteristic multiple cysteine-rich repeats within their extracellular domains, and do not possess catalytic motifs within cytoplasmic regions (Smith et al., 1994). The receptors signal through direct interactions with death domain proteins (e.g., TRADD, FADD, and RIP) or with the TRAF proteins (e.g., TRAF2, TRAF3, TRAF5, and TRAF6), triggering divergent and overlapping signaling pathways, e.g., apoptosis, NF-B activation, or JNK activation (Wallach et al., 1999, *Ann. Rev. Immunol.* 17: 331-67). These signaling events lead to cell death, proliferation, activation, or differentiation. The expression profile of each receptor member varies. For example, while TNFR1 is expressed in a broad spectrum of tissues and cell types, the cell surface receptor for OPGL is mainly restricted to the osteoclasts (Hsu et al., 1999, *Proc. Natl. Acad. Sci. U.S.A.* 96:3540-45).

The TNF family ligand TALL-1 is a type II transmembrane protein that is produced by cells of myeloid origin. TALL-1 is known to bind to two other members of the TNFR family: transmembrane activator and calcium modulator and cyclophilin ligand interactor (TACI) and B cell maturation antigen (BCMA). It is an object of the invention to identify nucleic acids encoding a receptor for TALL-1. Since TALL-1 is believed to play a role in inflammatory and immune processes, TALL-1R molecules would have wide application in the medical arts, particularly in treating autoimmune and inflammatory disorders.

SUMMARY OF THE INVENTION

The present invention relates to novel TALL-1R nucleic acid molecules and encoded polypeptides. The TALL-1R polypeptides of the present invention act as receptors for the TNF ligand TALL-1 (also designated as BAFF, THANK, BlyS, and zTNF4).

The invention provides for an isolated nucleic acid molecule comprising:

(a) the nucleotide sequence as set forth in any of SEQ ID NO: 1, SEQ ID NO: 3, or SEQ ID NO: 5;

(b) a nucleotide sequence encoding the polypeptide as set forth in any of SEQ ID NO: 2, SEQ ID NO: 4, SEQ ID NO: 6, SEQ ID NO: 7, or SEQ ID NO: 14;

(c) a nucleotide sequence that hybridizes under at least moderately stringent conditions to the complement of the nucleotide sequence of either (a) or (b), wherein the nucleic acid molecule encodes a polypeptide having an activity of the polypeptide set forth in any of SEQ ID NO: 2, SEQ ID NO: 4, SEQ ID NO: 6, SEQ ID NO: 7, or SEQ ID NO: 14; or (d) a nucleotide sequence complementary to the nucleotide sequence of any of (a)-(c).

The invention also provides for an isolated nucleic acid molecule comprising:

(a) a nucleotide sequence encoding a polypeptide that is at least about 87 percent identical to the polypeptide as set forth in any of SEQ ID NO: 2, SEQ ID NO: 4, SEQ ID NO: 6, or SEQ ID NO: 7, wherein the encoded polypeptide has an activity of the polypeptide set forth in any of SEQ ID NO: 2, SEQ ID NO: 4, SEQ ID NO: 6, or SEQ ID NO: 7;

(b) a nucleotide sequence encoding an allelic variant or splice variant of the nucleotide sequence as set forth in any of SEQ ID NO: 1, SEQ ID NO: 3, or SEQ ID NO: 5 or the nucleotide sequence of (a);

(c) a region of the nucleotide sequence of any of SEQ ID NO: 1, SEQ ID NO: 3, or SEQ ID NO: 5, or the nucleotide sequence of either (a) or (b), encoding a polypeptide fragment of at least about 25 amino acid residues, wherein the polypeptide fragment has an activity of the polypeptide as set forth in any of SEQ ID NO: 2, SEQ ID NO: 4, SEQ ID NO: 6, SEQ ID NO: 7, or SEQ ID NO: 14, or is antigenic;

(d) a region of the nucleotide sequence of any of SEQ ID NO: 1, SEQ ID NO: 3, or SEQ ID NO: 5 or the nucleotide sequence of any of (a)-(c) comprising a fragment of at least about 16 nucleotides;

(e) a nucleotide sequence that hybridizes under at least moderately stringent conditions to the complement of the nucleotide sequence of any of (a)-(d), wherein the nucleic acid molecule encodes a polypeptide having an activity of the polypeptide set forth in any of SEQ ID NO: 2, SEQ ID NO: 4, SEQ ID NO: 6, SEQ ID NO: 7, or SEQ ID NO: 14; or (f) a nucleotide sequence complementary to the nucleotide sequence of any of (a)-(e).

The invention further provides for an isolated nucleic acid molecule comprising:

(a) a nucleotide sequence encoding a polypeptide as set forth in any of SEQ ID NO: 2, SEQ ID NO: 4, SEQ ID NO: 6, SEQ ID NO: 7, or SEQ ID NO: 14 with at least one conservative amino acid substitution, wherein the encoded polypeptide has an activity of the polypeptide set forth in any of SEQ ID NO: 2, SEQ ID NO: 4, SEQ ID NO: 6, SEQ ID NO: 7, or SEQ ID NO: 14;

(b) a nucleotide sequence encoding a polypeptide as set forth in any of SEQ ID NO: 2, SEQ ID NO: 4, SEQ ID NO: 6, SEQ ID NO: 7, or SEQ ID NO: 14 with at least one amino acid insertion, wherein the encoded polypeptide has an activity of the polypeptide set forth in any of SEQ ID NO: 2, SEQ ID NO: 4, SEQ ID NO: 6, SEQ ID NO: 7, or SEQ ID NO: 14;

(c) a nucleotide sequence encoding a polypeptide as set forth in any of SEQ ID NO: 2, SEQ ID NO: 4, SEQ ID NO: 6, SEQ ID NO: 7, or SEQ ID NO: 14 with at least one amino acid deletion, wherein the encoded polypeptide has an activity of the polypeptide set forth in any of SEQ ID NO: 2, SEQ ID NO: 4, SEQ ID NO: 6, SEQ ID NO: 7, or SEQ ID NO: 14;

(d) a nucleotide sequence encoding a polypeptide as set forth in any of SEQ ID NO: 2, SEQ ID NO: 4, SEQ ID NO: 6, SEQ ID NO: 7, or SEQ ID NO: 14 that has a C- and/or N-terminal truncation, wherein the encoded polypeptide has an activity of the polypeptide set forth in any of SEQ ID NO: 2, SEQ ID NO: 4, SEQ ID NO: 6, SEQ ID NO: 7, or SEQ ID NO: 14;

(e) a nucleotide sequence encoding a polypeptide as set forth in any of SEQ ID NO: 2, SEQ ID NO: 4, SEQ ID NO: 6, SEQ ID NO: 7, or SEQ ID NO: 14 with at least one modification that is an amino acid substitution, amino acid insertion, amino acid deletion, C-terminal truncation, or N-terminal truncation, wherein the encoded polypeptide has an activity of the polypeptide set forth in any of SEQ ID NO: 2, SEQ ID NO: 4, SEQ ID NO: 6, SEQ ID NO: 7, or SEQ ID NO: 14;

(f) a nucleotide sequence of any of (a)-(e) comprising a fragment of at least about 16 nucleotides;

(g) a nucleotide sequence that hybridizes under at least moderately stringent conditions to the complement of the nucleotide sequence of any of (a)-(f), wherein the nucleic acid molecule encodes a polypeptide having an activity of the polypeptide set forth in any of SEQ ID NO: 2, SEQ ID NO: 4, SEQ ID NO: 6, SEQ ID NO: 7, or SEQ ID NO: 14; or (h) a nucleotide sequence complementary to the nucleotide sequence of any of (a)-(g).

The invention still further provides for an isolated nucleic acid molecule comprising:

(a) a region of the nucleotide sequence of any of SEQ ID NO: 1, SEQ ID NO: 3, or SEQ ID NO: 5, encoding a polypeptide fragment comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7;

(b) a region of the nucleotide sequence of either SEQ ID NO: 1 or SEQ ID NO: 3, encoding a polypeptide fragment comprising amino acid residues 1-84 of the amino acid sequence as set forth in any of SEQ ID NO: 2, SEQ ID NO: 4, or SEQ ID NO: 7; or (c) a region of the nucleotide sequence of SEQ ID NO: 5, encoding a polypeptide fragment comprising amino acid residues 1-83 of the amino acid sequence as set forth in SEQ ID NO: 6.

The invention still further provides for an isolated nucleic acid molecule comprising:

(a) a nucleotide sequence encoding a polypeptide comprising the amino acid sequence of SEQ ID NO: 14; or (b) a nucleotide sequence complementary to the nucleotide sequence of (a).

The present invention provides for an isolated polypeptide comprising the amino acid sequence set forth in any of SEQ ID NO: 2, SEQ ID NO: 4, SEQ ID NO: 6, SEQ ID NO: 7, or SEQ ID NO: 14.

The invention also provides for an isolated polypeptide comprising:

(a) an amino acid sequence for an ortholog of any of SEQ ID NO: 2, SEQ ID NO: 4, SEQ ID NO: 6, SEQ ID NO: 7, or SEQ ID NO: 14;

(b) an amino acid sequence which is at least about 87 percent identical to the amino acid sequence of any of SEQ ID NO: 2, SEQ ID NO: 4, SEQ ID NO: 6, or SEQ ID NO: 7, wherein the polypeptide has an activity of the polypeptide set forth in any of SEQ ID NO: 2, SEQ ID NO: 4, SEQ ID NO: 6, or SEQ ID NO: 7;

(c) a fragment of the amino acid sequence set forth in any of SEQ ID NO: 2, SEQ ID NO: 4, SEQ ID NO: 6, SEQ ID NO: 7, or SEQ ID NO: 14 comprising at least about 25 amino acid residues, wherein the fragment has an activity of the polypeptide set forth in any of SEQ ID NO: 2, SEQ ID NO: 4, SEQ ID NO: 6, SEQ ID NO: 7, or SEQ ID NO: 14, or is antigenic; or (d) an amino acid sequence for an allelic variant or splice variant of the amino acid sequence as set forth in any of SEQ ID NO: 2, SEQ ID NO: 4, SEQ ID NO: 6, SEQ ID NO: 7, or SEQ ID NO: 14, or the amino acid sequence of either (a) or (b).

The invention further provides for an isolated polypeptide comprising:

(a) the amino acid sequence as set forth in any of SEQ ID NO: 2, SEQ ID NO: 4, SEQ ID NO: 6, SEQ ID NO: 7, or SEQ ID NO: 14 with at least one conservative amino acid substitution, wherein the polypeptide has an activity of the polypeptide set forth in any of SEQ ID NO: 2, SEQ ID NO: 4, SEQ ID NO: 6, SEQ ID NO: 7, or SEQ ID NO: 14;

(b) the amino acid sequence as set forth in any of SEQ ID NO: 2, SEQ ID NO: 4, SEQ ID NO: 6, SEQ ID NO: 7, or SEQ ID NO: 14 with at least one amino acid insertion, wherein the polypeptide has an activity of the polypeptide set forth in any of SEQ ID NO: 2, SEQ ID NO: 4, SEQ ID NO: 6, SEQ ID NO: 7, or SEQ ID NO: 14;

(c) the amino acid sequence as set forth in any of SEQ ID NO: 2, SEQ ID NO: 4, SEQ ID NO: 6, SEQ ID NO: 7, or SEQ ID NO: 14 with at least one amino acid deletion, wherein the polypeptide has an activity of the polypeptide set forth in any of SEQ ID NO: 2, SEQ ID NO: 4, SEQ ID NO: 6, SEQ ID NO: 7, or SEQ ID NO: 14;

(d) the amino acid sequence as set forth in any of SEQ ID NO: 2, SEQ ID NO: 4, SEQ ID NO: 6, SEQ ID NO: 7, or SEQ ID NO: 14 that has a C- and/or N-terminal truncation, wherein the polypeptide has an activity of the polypeptide set forth in any of SEQ ID NO: 2, SEQ ID NO: 4, SEQ ID NO: 6, SEQ ID NO: 7, or SEQ ID NO: 14; or (e) the amino acid sequence as set forth in any of SEQ ID NO: 2, SEQ ID NO: 4, SEQ ID NO: 6, SEQ ID NO: 7, or SEQ ID NO: 14 with at least one modification that is an amino acid substitution, amino acid insertion, amino acid deletion, C-terminal truncation, or N-terminal truncation, wherein the polypeptide has an activity of the polypeptide set forth in any of SEQ ID NO: 2, SEQ ID NO: 4, SEQ ID NO: 6, SEQ ID NO: 7, or SEQ ID NO: 14.

The invention still further provides for an isolated polypeptide comprising:

(a) an amino acid sequence comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7;

(b) an amino acid sequence comprising amino acid residues 1-84 of the amino acid sequence as set forth in any of SEQ ID NO: 2, SEQ ID NO: 4, or SEQ ID NO: 7; or (c) an amino acid sequence comprising amino acid residues 1-83 of the amino acid sequence as set forth in SEQ ID NO: 6.

The invention still further provides for an polypeptide comprising the amino acid sequence of SEQ ID NO: 14.

Also provided are fusion polypeptides comprising TALL-1R amino acid sequences.

The present invention also provides for an expression vector comprising the isolated nucleic acid molecules as set forth herein, recombinant host cells comprising the recombinant nucleic acid molecules as set forth herein, and a method of producing a TALL-1R polypeptide comprising culturing the host cells and optionally isolating the polypeptide so produced.

A transgenic non-human animal comprising a nucleic acid molecule encoding a TALL-1R polypeptide is also encompassed by the invention. The TALL-1R nucleic acid molecules are introduced into the animal in a manner that allows expression and increased levels of a TALL-1R polypeptide, which may include increased circulating levels. Alternatively, the TALL-1R nucleic acid molecules are introduced into the animal in a manner that prevents expression of endogenous TALL-1R polypeptide (i.e., generates a transgenic animal possessing a TALL-1R polypeptide gene knockout). The transgenic non-human animal is preferably a mammal, and more preferably a rodent, such as a rat or a mouse.

Also provided are derivatives of the TALL-1R polypeptides of the present invention.

Additionally provided are selective binding agents such as antibodies and peptides capable of specifically binding the TALL-1R polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The TALL-1R polypeptides and nucleic acid molecules of the present invention may be used to treat, prevent, ameliorate, and/or detect diseases and disorders, including those recited herein.

The present invention also provides a method of assaying test molecules to identify a test molecule that binds to a TALL-1R polypeptide. The method comprises contacting a TALL-1R polypeptide with a test molecule to determine the extent of binding of the test molecule to the polypeptide. The method further comprises determining whether such test molecules are agonists or antagonists of a TALL-1R polypeptide. The present invention further provides a method of testing the impact of molecules on the expression of TALL-1R polypeptide or on the activity of TALL-1R polypeptide.

Methods of regulating expression and modulating (i.e., increasing or decreasing) levels of a TALL-1R polypeptide are also encompassed by the invention. One method comprises administering to an animal a nucleic acid molecule encoding a TALL-1R polypeptide. In another method, a nucleic acid molecule comprising elements that regulate or modulate the expression of a TALL-1R polypeptide may be administered. Examples of these methods include gene therapy, cell therapy, and anti-sense therapy as further described herein.

In another aspect of the present invention, TALL-1 R polypeptides can be used for identifying ligands thereof. Various forms of "expression cloning" have been used for cloning ligands for receptors (See, e.g., Davis et al., 1996, *Cell*, 87:1161-69). These and other TALL-1R ligand cloning experiments are described in greater detail herein. Isolation of the TALL-1R ligand(s) allows for the identification or development of novel agonists and/or antagonists of the TALL-1R signaling pathway. Such agonists and antagonists include TALL-1R ligand(s), anti-TALL-1R ligand antibodies and derivatives thereof, small molecules, or antisense oligonucleotides, any of which can be used for potentially treating one or more diseases or disorders, including those recited herein.

BRIEF DESCRIPTION OF THE FIGURES

FIG. 5 illustrates a nucleotide sequence (clone 710; SEQ ID NO: 1) encoding a human TALL-1R polypeptide (SEQ ID NO: 2);

FIG. 6 illustrates a nucleotide sequence (clone 711; SEQ ID NO: 3) encoding a human TALL-1R polypeptide (SEQ ID NO: 4);

FIG. 7 illustrates a nucleotide sequence (clone 706; SEQ ID NO: 5) encoding a human TALL-1R polypeptide (SEQ ID NO: 6);

FIG. 8A illustrates an amino acid sequence alignment of human TALL-1R polypeptides encoded by clone 711 (SEQ ID NO: 4), clone 713 (SEQ ID NO: 7), clone 706 (SEQ ID NO: 6), and clone 710 (SEQ ID NO: 2);

FIG. 8B illustrates a TALL-1R amino acid sequence (SEQ ID NO: 14) derived from the amino acid sequence alignment illustrated in FIG. 8A;

DETAILED DESCRIPTION OF THE INVENTION

Figure 1A:
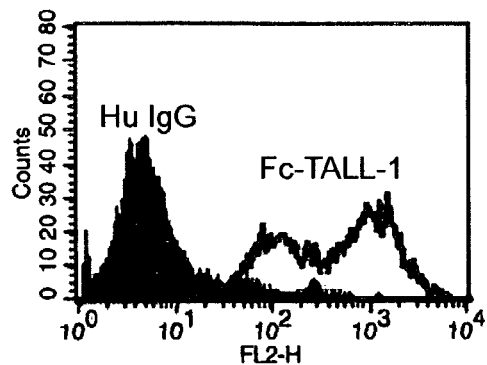
FIGS. 1A-1D show the results of FACS analysis of 293 cells transfected with either TACI (FIGS. 1A and 1B) or BCMA (FIGS. 1C and 1D) expression vectors, following incubation with either Fc-TALL-1 (FIGS. 1A and 1C), anti-TACI antibody (FIG. B), or anti-BCMA antibody (FIG. D)

The section headings used herein are for organizational purposes only and are not to be construed as limiting the subject matter described. All references cited in this application are expressly incorporated by reference herein.

Definitions

The terms "TALL-1R gene" or "TALL-1R nucleic acid molecule" or "TALL-1R polynucleotide" refer to a nucleic acid molecule comprising or consisting of a nucleotide sequence as set forth in any of SEQ ID NO: 1, SEQ ID NO: 3, or SEQ ID NO: 5, a nucleotide sequence encoding the polypeptide as set forth in any of SEQ ID NO: 2, SEQ ID NO: 4, SEQ ID NO: 6, or SEQ ID NO: 7, and nucleic acid molecules as defined herein. The term "TALL-1R gene" also refers to a nucleic acid molecule comprising a nucleotide sequence encoding a polypeptide as set forth in SEQ ID NO: 14.

The term "TALL-1R polypeptide allelic variant" refers to one of several possible naturally occurring alternate forms of a gene occupying a given locus on a chromosome of an organism or a population of organisms.

The term "TALL-1R polypeptide splice variant" refers to a nucleic acid molecule, usually RNA, which is generated by alternative processing of intron sequences in an RNA transcript of TALL-1R polypeptide amino acid sequence as set forth in any of SEQ ID NO: 2, SEQ ID NO: 4, SEQ ID NO: 6, SEQ ID NO: 7, or SEQ ID NO: 14.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "TALL-1R polypeptide" refers to a polypeptide comprising the amino acid sequence of any of SEQ ID NO: 2, SEQ ID NO: 4, SEQ ID NO: 6, or SEQ ID NO: 7 and related polypeptides. Related polypeptides include TALL-1R polypeptide fragments, TALL-1R polypeptide orthologs, TALL-1R polypeptide variants, and TALL-1R polypeptide derivatives, which possess at least one activity of the polypeptide as set forth in any of SEQ ID NO: 2, SEQ ID NO: 4, SEQ ID NO: 6, or SEQ ID NO: 7. The term "TALL-1R polypeptide" also refers to a polypeptide comprising the amino acid sequence as set forth in SEQ ID NO: 14. TALL-1R polypeptides may be mature polypeptides, as defined herein, and may or may not have an amino-terminal methionine residue, depending on the method by which they are prepared.

The term "TALL-1R polypeptide fragment" refers to a polypeptide that comprises a truncation at the amino-terminus (with or without a leader sequence) and/or a truncation at the carboxyl-terminus of the polypeptide as set forth in any of SEQ ID NO: 2, SEQ ID NO: 4, SEQ ID NO: 6, SEQ ID NO: 7, or SEQ ID NO: 14. The term "TALL-1R polypeptide fragment" also refers to amino-terminal and/or carboxyl-terminal truncations of TALL-1R polypeptide orthologs, TALL-1R polypeptide derivatives, or TALL-1R polypeptide variants, or to amino-terminal and/or carboxyl-terminal truncations of the polypeptides encoded by TALL-1R polypeptide allelic variants or TALL-1R polypeptide splice variants. TALL-1R polypeptide fragments may result from alternative RNA splicing or from in vivo protease activity. Membrane-bound forms of a TALL-1R polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or more than about 100 amino acids. Such TALL-1R polypeptide fragments may optionally comprise an amino-terminal methionine residue. It will be appreciated that such fragments can be used, for example, to generate antibodies to TALL-1R polypeptides. Preferred TALL-1R polypeptide fragments include polypeptide fragments comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7; amino acid residues 1-84 of the amino acid sequence as set forth in any of SEQ ID NO:

2, SEQ ID NO: 4, or SEQ ID NO: 7; and amino acid residues 1-83 of the amino acid sequence as set forth in SEQ ID NO: 6.

The term "TALL-1R polypeptide ortholog" refers to a polypeptide from another species that corresponds to TALL-1R polypeptide amino acid sequence as set forth in any of SEQ ID NO: 2, SEQ ID NO: 4, SEQ ID NO: 6, SEQ ID NO: 7, or SEQ ID NO: 14. For example, mouse and human TALL-1R polypeptides are considered orthologs of each other.

The term "TALL-1R polypeptide variants" refers to TALL-1R polypeptides comprising amino acid sequences having one or more amino acid sequence substitutions, deletions (such as internal deletions and/or TALL-1R polypeptide fragments), and/or additions (such as internal additions and/or TALL-1R fusion polypeptides) as compared to the TALL-1R polypeptide amino acid sequence set forth in any of SEQ ID NO: 2, SEQ ID NO: 4, SEQ ID NO: 6, SEQ ID NO: 7, or SEQ ID NO: 14 (with or without a leader sequence). Variants may be naturally occurring (e.g., TALL-1R polypeptide allelic variants, TALL-1R polypeptide orthologs, and TALL-1R polypeptide splice variants) or artificially constructed. Such TALL-1R polypeptide variants may be prepared from the corresponding nucleic acid molecules having a DNA sequence that varies accordingly from the DNA sequence as set forth in any of SEQ ID NO: 1, SEQ ID NO: 3, or SEQ ID NO: 5. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "TALL-1R polypeptide derivatives" refers to the polypeptide as set forth in any of SEQ ID NO: 2, SEQ ID NO: 4, SEQ ID NO: 6, SEQ ID NO: 7, or SEQ ID NO: 14, TALL-1R polypeptide fragments, TALL-1R polypeptide orthologs, or TALL-1R polypeptide variants, as defined herein, that have been chemically modified. The term "TALL-1R polypeptide derivatives" also refers to the polypeptides encoded by TALL-1R polypeptide allelic variants or TALL-1R polypeptide splice variants, as defined herein, that have been chemically modified.

The term "mature TALL-1R polypeptide" refers to a TALL-1R polypeptide lacking a leader sequence. A mature TALL-1R polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like.

The term "TALL-1R fusion polypeptide" refers to a fusion of one or more amino acids (such as a heterologous protein or peptide) at the amino- or carboxyl-terminus of the polypeptide as set forth in any of SEQ ID NO: 2, SEQ ID NO: 4, SEQ ID NO: 6, SEQ ID NO: 7, or SEQ ID NO: 14, TALL-1R polypeptide fragments, TALL-1R polypeptide orthologs, TALL-1R polypeptide variants, or TALL-1R derivatives, as defined herein. The term "TALL-1R fusion polypeptide" also refers to a fusion of one or more amino acids at the amino- or carboxyl-terminus of the polypeptide encoded by TALL-1R polypeptide allelic variants or TALL-1R polypeptide splice variants, as defined herein.

The term "biologically active TALL-1R polypeptides" refers to TALL-1R polypeptides having at least one activity characteristic of the polypeptide comprising the amino acid sequence of any of SEQ ID NO: 2, SEQ ID NO: 4, SEQ ID NO: 6, SEQ ID NO: 7, or SEQ ID NO: 14. In addition, a TALL-1R polypeptide may be active as an immunogen; that is, the TALL-1R polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness that includes both identical matches and conservative substitution matches. If two polypeptide sequences have, for example, $10/20$ identical amino acids, and the remainder are all non-conservative substitutions, then the percent identity and similarity would both be 50%. If in the same example, there are five more positions where there are conservative substitutions, then the percent identity remains 50%, but the percent similarity would be 75% ($15/20$). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man. When used in connection with nucleotides, the terms "naturally occurring" or "native" refer to the bases adenine (A), cytosine (C), guanine (G), thymine (T), and uracil (U). When used in connection with amino acids, the terms "naturally occurring" and "native" refer to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (O), arginine (R), serine (S), threonine (T), valine (V), tryptophan (W), and tyrosine (Y).

The terms "effective amount" and "therapeutically effective amount" each refer to the amount of a TALL-1R polypeptide or TALL-1R nucleic acid molecule used to support an observable level of one or more biological activities of the TALL-1R polypeptides as set forth herein.

The term "pharmaceutically acceptable carrier" or "physiologically acceptable carrier" as used herein refers to one or more formulation materials suitable for accomplishing or enhancing the delivery of the TALL-1R polypeptide, TALL-1R nucleic acid molecule, or TALL-1R selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a TALL-1R polypeptide. As used herein, the terms, "specific" and "specificity" refer to the ability of the selective binding agents to bind to human TALL-1R polypeptides and not to bind to human non-TALL-1R polypeptides. It will be appreciated, however, that the selective binding agents may also bind orthologs of the polypeptide as set forth in any of SEQ ID NO: 2, SEQ ID NO: 4, SEQ ID NO: 6, SEQ ID NO: 7, or SEQ ID NO: 14, that is, interspecies versions thereof, such as mouse and rat TALL-1R polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al, 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of any of SEQ ID NO: 1, SEQ ID NO: 3, or SEQ ID NO: 5, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide set orth in any of SEQ ID NO: 2, SEQ ID NO: 4, SEQ ID NO: 6, SEQ ID NO: 7, or SEQ ID NO: 14. Such related TALL-1R polypeptides may comprise, for example, an addition and/or a deletion of one or more N-linked or O-linked glycosylation sites or an addition and/or a deletion of one or more cysteine residues.

Related nucleic acid molecules also include fragments of TALL-1R nucleic acid molecules which encode a polypeptide of at least about 25 contiguous amino acids, or about 50 amino acids, or about 75 amino acids, or about 100 amino acids, or more than about 100 amino acid residues of the TALL-1R polypeptide of any of SEQ ID NO: 2, SEQ ID NO: 4, SEQ ID NO: 6, SEQ ID NO: 7, or SEQ ID NO: 14.

In addition, related TALL-1R nucleic acid molecules also include those molecules which comprise nucleotide sequences which hybridize under moderately or highly stringent conditions as defined herein with the fully complementary sequence of the TALL-1R nucleic acid molecule of any of SEQ ID NO: 1, SEQ ID NO: 3, or SEQ ID NO: 5, or of a molecule encoding a polypeptide, which polypeptide comprises the amino acid sequence as shown in any of SEQ ID NO: 2, SEQ ID NO: 4, SEQ ID NO: 6, SEQ ID NO: 7, or SEQ ID NO: 14, or of a nucleic acid fragment as defined herein, or of a nucleic acid fragment encoding a polypeptide as defined herein. Hybridization probes may be prepared using the TALL-1R sequences provided herein to screen cDNA, genomic or synthetic DNA libraries for related sequences. Regions of the DNA and/or amino acid sequence of TALL-1R polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecyl-sulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2° C. \text{ per } A-T \text{ base pair}+4° C. \text{ per } G-C \text{ base pair}$$

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 87 percent identical to the nucleotide sequence as shown in any of SEQ ID NO: 1, SEQ ID NO: 3, or SEQ ID NO: 5. In preferred embodiments, the nucleotide sequences are about 90 percent, or about 95, 96, 97, 98, or 99 percent identical to the nucleotide sequence as shown in any of SEQ ID NO: 1, SEQ ID NO: 3, or SEQ ID NO: 5. Related nucleic acid molecules encode polypeptides possessing at least one activity of the polypeptide set forth in any of SEQ ID NO: 2, SEQ ID NO: 4, SEQ ID NO: 6, SEQ ID NO: 7, or SEQ ID NO: 14. In further embodiments, related nucleic acid molecules comprise or consist of a nucleotide sequence encoding a TALL-1R polypeptide fragment that is at least about 87 percent identical to amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7; amino acid residues 1-84 of the amino acid sequence as set forth in any of SEQ ID NO: 2, SEQ ID NO: 4, or SEQ ID NO: 7; or amino acid residues 1-83 of the amino acid sequence as set forth in SEQ ID NO: 6. In preferred embodiments, related nucleic acid molecules comprise or consist of a nucleotide sequence encoding a TALL-1R polypeptide fragment that is at least about 90 percent, or about 95, 96, 97, 98, or 99 percent identical to amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7; amino acid residues 1-84 of the amino acid sequence as set forth in any of SEQ ID NO: 2, SEQ ID NO: 4, or SEQ ID NO: 7; or amino acid residues 1-83 of the amino acid sequence as set forth in SEQ ID NO: 6.

Differences in the nucleic acid sequence may result in conservative and/or non-conservative modifications of the amino acid sequence relative to the amino acid sequence of any of SEQ ID NO: 2, SEQ ID NO: 4, SEQ ID NO: 6, or SEQ ID NO: 7.

Conservative modifications to the amino acid sequence of any of SEQ ID NO: 2, SEQ ID NO: 4, SEQ ID NO: 6, SEQ ID NO: 7, or SEQ ID NO: 14 (and the corresponding modifications to the encoding nucleotides) will produce a polypeptide having functional and chemical characteristics similar to those of TALL-1R polypeptides. In contrast, substantial modifications in the functional and/or chemical characteristics of TALL-1R polypeptides may be accomplished by selecting substitutions in the amino acid sequence of any of SEQ ID NO: 2, SEQ ID NO: 4, SEQ ID NO: 6, SEQ ID NO: 7, or SEQ ID NO: 14 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human TALL-1R polypeptide that are homologous with non-human TALL-1R polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the TALL-1R polypeptide, or to increase or decrease the affinity of the TALL-1R polypeptides described herein. Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |

TABLE I-continued

Amino Acid Substitutions

| Original Residues | Exemplary Substitutions | Preferred Substitutions |
|---|---|---|
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NO: 2, SEQ ID NO: 4, SEQ ID NO: 6, SEQ ID NO: 7, or SEQ ID NO: 14 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a TALL-1R polypeptide to such similar polypeptides. With such a comparison, one can identify residues and portions of the molecules that are conserved among similar polypeptides. It will be appreciated that changes in areas of the TALL-1R molecule that are not conserved relative to such similar polypeptides would be less likely to adversely affect the biological activity and/or structure of a TALL-1R polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a TALL-1R polypeptide that correspond to amino acid residues that are important for activity or structure in similar polypeptides. One skilled in the art may opt for chemically similar amino acid substitutions for such predicted important amino acid residues of TALL-1R polypeptides.

One skilled in the art can also analyze the three-dimensional structure and amino acid sequence in relation to that structure in similar polypeptides. In view of such information, one skilled in the art may predict the alignment of amino acid residues of TALL-1R polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al, 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred TALL-1R polypeptide variants include glycosylation variants wherein the number and/or type of glycosylation sites have been altered compared to the amino acid sequence set forth in any of SEQ ID NO: 2, SEQ ID NO: 4, SEQ ID NO: 6, SEQ ID NO: 7, or SEQ ID NO: 14. In one embodiment, TALL-1R polypeptide variants comprise a greater or a lesser number of N-linked glycosylation sites than the amino acid sequence set forth in any of SEQ ID NO: 2, SEQ ID NO: 4, SEQ ID NO: 6, SEQ ID NO: 7, or SEQ ID NO: 14. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred TALL-1R variants include cysteine variants, wherein one or more cysteine residues are deleted or substituted with another amino acid (e.g., serine) as compared to the amino acid sequence set forth in any of SEQ ID NO: 2, SEQ ID NO: 4, SEQ ID NO: 6, SEQ ID NO: 7, or SEQ ID NO: 14. Cysteine variants are useful when TALL-1R polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, TALL-1R polypeptide variants comprise an amino acid sequence as set forth in any of SEQ ID NO: 2, SEQ ID NO: 4, SEQ ID NO: 6, SEQ ID NO: 7, or SEQ ID NO: 14 with at least one amino acid insertion and wherein the polypeptide has an activity of the polypeptide set forth in any of SEQ ID NO: 2, SEQ ID NO: 4, SEQ ID NO: 6, SEQ ID NO: 7, or SEQ ID NO: 14, or an amino acid sequence encoding a polypeptide as set forth in any of SEQ ID NO: 2, SEQ ID NO: 4, SEQ ID NO: 6, SEQ ID NO: 7, or SEQ ID NO: 14 with at least one amino acid deletion and wherein the polypeptide has an activity of the polypeptide set forth in any of SEQ ID NO: 2, SEQ ID NO: 4, SEQ ID NO: 6, SEQ ID NO: 7, or SEQ ID NO: 14. TALL-1R polypeptide variants also comprise an amino acid sequence as set forth in any of SEQ ID NO: 2, SEQ ID NO: 4, SEQ ID NO: 6, SEQ ID NO: 7, or SEQ ID NO: 14 wherein the polypeptide has a carboxyl- and/or amino-terminal truncation and further wherein the polypeptide has an activity of the polypeptide set forth in any of SEQ ID NO: 2, SEQ ID NO: 4, SEQ ID NO: 6, SEQ ID NO: 7, or SEQ ID NO: 14. TALL-1R polypeptide variants further comprise an amino acid sequence as set forth in any of SEQ ID NO: 2, SEQ ID NO: 4, SEQ ID NO: 6, SEQ ID NO: 7, or SEQ ID NO: 14 with at least one modification that is an amino acid substitution, amino acid insertion, amino acid deletion, carboxyl-terminal truncation, or amino-terminal truncation, and wherein the polypeptide has an activity of the polypeptide set forth in any of SEQ ID NO: 2, SEQ ID NO: 4, SEQ ID NO: 6, SEQ ID NO: 7, or SEQ ID NO: 14.

In further embodiments, TALL-1R polypeptide variants comprise an amino acid sequence that is at least about 87 percent identical to the amino acid sequence as set forth in any of SEQ ID NO: 2, SEQ ID NO: 4, SEQ ID NO: 6, or SEQ ID NO: 7. In preferred embodiments, TALL-1R polypeptide variants comprise an amino acid sequence that is at least about 90 percent, or about 95, 96, 97, 98, or 99 percent identical to the amino acid sequence as set forth in any of SEQ ID NO: 2, SEQ ID NO: 4, SEQ ID NO: 6, or SEQ ID NO: 7. TALL-1R polypeptide variants possess at least one activity of the polypeptide set forth in any of SEQ ID NO: 2, SEQ ID NO: 4, SEQ ID NO: 6, or SEQ ID NO: 7.

In still further embodiments, TALL-1R polypeptide variants comprise an amino acid sequence that is at least about 87 percent identical to amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7; amino acid residues 1-84 of the amino acid sequence as set forth in any of SEQ ID NO: 2, SEQ ID NO: 4, or SEQ ID NO: 7; or amino acid residues 1-83 of the amino acid sequence as set forth in SEQ ID NO: 6. In preferred embodiments, TALL-1R polypeptide variants comprise an amino acid sequence that is at least about 90 percent, or about 95, 96, 97, 98, or 99 percent identical to amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7; amino acid residues 1-84 of the amino acid sequence as set forth in any of SEQ ID NO: 2, SEQ ID NO: 4, or SEQ ID NO: 7; or amino acid residues 1-83 of the amino acid sequence as set forth in SEQ ID NO: 6.

In addition, the polypeptide comprising the amino acid sequence of any of SEQ ID NO: 2, SEQ ID NO: 4, SEQ ID NO: 6, SEQ ID NO: 7, or SEQ ID NO: 14, or other TALL-1R polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a TALL-1R fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in any of SEQ ID NO: 2, SEQ ID NO: 4, SEQ ID NO: 6, SEQ ID NO: 7, or SEQ ID NO: 14, or other TALL-1R polypeptide.

Fusions can be made either at the amino-terminus or at the carboxyl-terminus of the polypeptide comprising the amino acid sequence set forth in any of SEQ ID NO: 2, SEQ ID NO: 4, SEQ ID NO: 6, SEQ ID NO: 7, or SEQ ID NO: 14, or other TALL-1R polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of any of SEQ ID NO: 2, SEQ ID NO: 4, SEQ ID NO: 6, SEQ ID NO: 7, or SEQ ID NO: 14, or other TALL-1R polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, Nature 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590–600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |

TABLE II-continued

Fc Fusion with Therapeutic Proteins

| Form of Fc | Fusion partner | Therapeutic implications | Reference |
|---|---|---|---|
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | International Pub. No. WO 97/23614 |
| IgG1 | N-terminus of leptin | anti-obesity | International Pub. No. WO 98/28427 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the amino-terminus or carboxyl-terminus of the TALL-1R polypeptides using methods known to the skilled artisan. In another example, a human IgG hinge, CH2, and CH3 region may be fused at either the amino-terminus or carboxyl-terminus of a TALL-1R polypeptide fragment (e.g., the predicted extracellular portion of TALL-1R polypeptide).

The resulting TALL-1R fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Useful modifications of protein therapeutic agents by fusion with the "Fc" domain of an antibody are discussed in detail in U.S. patent application Ser. No. 09/428,082 (International Pub. No. WO 99/25044), which is hereby incorporated by reference in its entirety. That patent application discusses linkage to a "vehicle" such as polyethylene gycol (PEG), dextran, or an Fc region.

In the compositions of matter prepared in accordance with this invention, a TALL-1R polypeptide may be attached to a vehicle through the polypeptide's N-terminus or C-terminus. Thus, the vehicle-polypeptide molecules of this invention may be described by the formula $(X^1)_a$—$F^1$—$(X^2)_b$ (I) wherein:

$F^1$ is a vehicle (preferably an Fc domain);

$X^1$ and $X^2$ are each independently selected from -$(L^1)_c$-$P^1$-$(L^1)_c$-$P^1$-$(L^2)_d$-$P^2$, -$(L^1)_c$-$P^1$-$(L^2)_d$-$P^2$-$(L^3)_e$-$P^3$, and -$(L^1)_c$- $P^1$-$(L^2)_d$-$P^2$-$(L^3)_e$-$P^3$-$(L^4)_f$-$P^4$;

$P^1$, $P^2$, $P^3$, and $P^4$ are each independently sequences of a TALL-1R polypeptide and are preferably selected from SEQ ID NO: 2, SEQ ID NO: 4, SEQ ID NO: 6, SEQ ID NO: 7, or SEQ ID NO: 14;

$L^1$, $L^2$, $L^3$, and $L^4$ are each independently linkers; and a, b, c, d, e, and f are each independently 0 or 1, provided that at least one of a and b is 1.

Thus, compound I comprises preferred compounds of the formulae: $X^1$—$F^1$ (II) and multimers thereof wherein $F^1$ is an Fc domain and is attached at the C-terminus of $X^1$; $F^1$—$X^2$ (III) and multimers thereof wherein $F^1$ is an Fc domain and is attached at the N-terminus of $X^2$; $F^1$-$(L^1)_c$-$P^1$(IV) and multimers thereof wherein $F^1$ is an Fc domain and is attached at the N-terminus of -$(L^1)_c$-$P^1$; and $F^1$-$(L^1)_c$-$P^1$-$(L^2)_d$-$P^2$ (V) and multimers thereof wherein $F^1$ is an Fc domain and is attached at the N-terminus of -$L^1$-$P^1$-$L^2$-$P^2$.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heijne, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.,* 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al, 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;

Comparison matrix: BLOSUM 62 (Henikoff et al., supra);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a TALL-1R polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a TALL-1R polypeptide has been identified from one species, all or a portion of that gene may be used as a probe to identify orthologs or related genes from the same species. The probes or primers may be used to screen cDNA libraries from various tissue sources believed to express the TALL-1R polypeptide. In addition, part or all of a nucleic acid molecule having the sequence as set forth in any of SEQ ID NO: 1, SEQ ID NO: 3, or SEQ ID NO: 5 may be used to screen a genomic library to identify and isolate a gene encoding the amino acid sequence of a TALL-1R polypeptide. Typically, conditions of moderate or high stringency will be employed for screening to minimize the number of false positives obtained from the screening.

Nucleic acid molecules encoding the amino acid sequence of TALL-1R polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a TALL-1R polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a TALL-1R polypeptide can be inserted into an expression vector. By introducing the expression vector into an appropriate host, the encoded TALL-1R polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of a TALL-1R polypeptide, are then added to the cDNA along with a polymerase such as Taq polymerase, and the polymerase amplifies the cDNA region between the two primers.

Another means of preparing a nucleic acid molecule encoding the amino acid sequence of a TALL-1R polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a TALL-1R polypeptide will be several hundred nucleotides in length. Nucleic acids larger than about 100 nucleotides can be synthesized as several fragments using these methods. The fragments can then be ligated together to form the full-length nucleotide sequence of a TALL-1R gene. Usually, the DNA fragment encoding the amino-terminus of the polypeptide will have an ATG, which encodes a methionine residue. This methionine may or may not be present on the mature form of the TALL-1R polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a TALL-1R polypeptide in a given host cell. Particular codon alterations will depend upon the TALL-1R polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "Drosophila_high.cod," "Human_high.cod," "Maize_high.cod," and "Yeast_high.cod."

In some cases, it may be desirable to prepare nucleic acid molecules encoding TALL-1R polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques).

Chemical synthesis using methods described by Engels et al., supra, may also be used to prepare such variants. Other methods known to the skilled artisan may be used as well.

Vectors and Host Cells

A nucleic acid molecule encoding the amino acid sequence of a TALL-1R polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a TALL-1R polypeptide may be amplified/expressed in prokaryotic, yeast, insect (baculovirus systems) and/or eukaryotic host cells. Selection of the host cell will depend in part on whether a TALL-1R polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the TALL-1R polypeptide coding sequence; the oligonucleotide sequence encodes polyHis (such as hexa-His), or another "tag" such as FLAG, HA (hemaglutinin influenza virus), or myc for which commercially available antibodies exist. This tag is typically fused to the polypeptide upon expression of the polypeptide, and can serve as a means for affinity purification of the TALL-1R polypeptide from the host cell. Affinity purification can be accomplished, for example, by column chromatography using antibodies against the tag as an affinity matrix. Optionally, the tag can subsequently be removed from the purified TALL-1R polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences that normally function to regulate TALL-1R polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the TALL-1R gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a TALL-1R polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a TALL-1R polypeptide. As a result, increased quantities of TALL-1R polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a TALL-1R polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a TALL-1R polypeptide out of the host cell. Typically, a nucleotide sequence encoding the signal sequence is positioned in the coding region of a TALL-1R nucleic acid molecule, or directly at the 5' end of a TALL-1R polypeptide coding region. Many signal sequences have been identified, and any of those that are functional in the selected host cell may be used in conjunction with a TALL-1R nucleic acid molecule. Therefore, a signal sequence may be homologous (naturally occurring) or heterologous to the TALL-1R nucleic acid molecule. Additionally, a signal sequence may be chemically synthesized using methods described herein. In most cases, the secretion of a TALL-1R polypeptide from the host cell via the presence of a signal peptide will result in the removal of the signal peptide from the secreted TALL-1R polypeptide. The signal sequence may be a component of the vector, or it may be a part of a TALL-1R nucleic acid molecule that is inserted into the vector.

Included within the scope of this invention is the use of either a nucleotide sequence encoding a native TALL-1R polypeptide signal sequence joined to a TALL-1R polypeptide coding region or a nucleotide sequence encoding a heterologous signal sequence joined to a TALL-1R polypeptide coding region. The heterologous signal sequence selected should be one that is recognized and processed, i.e., cleaved by a signal peptidase, by the host cell. For prokaryotic host cells that do not recognize and process the native TALL-1R polypeptide signal sequence, the signal sequence is substituted by a prokaryotic signal sequence selected, for example, from the group of the alkaline phosphatase, penicillinase, or heat-stable enterotoxin II leaders. For yeast secretion, the native TALL-1R polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired TALL-1R polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the TALL-1R gene especially where the gene used is a full-length genomic sequence or a fragment thereof. Where the intron is not naturally occurring within the gene (as for most cDNAs), the intron may be obtained from another source. The position of the intron with respect to flanking sequences and the TALL-1R gene is generally important, as the intron must be transcribed to be effective. Thus, when a TALL-1R cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the TALL-1R polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding TALL-1R polypeptide by removing the promoter from the source DNA by restriction enzyme digestion and inserting the desired promoter sequence into the vector. The native TALL-1R promoter sequence may be used to direct amplification and/or expression of a TALL-1R nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling TALL-1R gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al, 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al, 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al, 1987, *Genes and Devel.* 1:268-76); the alpha-feto-protein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a TALL-1R polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a TALL-1R nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pCRII, pCR3, and pcDNA3.1 (Invitrogen, Carlsbad, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (International Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives; Invitrogen), and mammalian, yeast or virus vectors such as a baculovirus expression system (pBacPAK plasmid derivatives; Clontech, Palo Alto, Calif.).

After the vector has been constructed and a nucleic acid molecule encoding a TALL-1R polypeptide has been inserted into the proper site of the vector, the completed vector may be inserted into a suitable host cell for amplification and/or polypeptide expression. The transformation of an expression vector for a TALL-1R polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a TALL-1R polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques,* 14:810-17; Lucklow, 1993, *Curr. Opin. Biotechnol.* 4:564-72; and Lucklow et al., 1993, *J. Virol.,* 67:4566-79. Preferred insect cells are Sf-9 and Hi5 (Invitrogen).

One may also use transgenic animals to express glycosylated TALL-1R polypeptides. For example, one may use a transgenic milk-producing animal (a cow or goat, for example) and obtain the present glycosylated polypeptide in the animal milk. One may also use plants to produce TALL-1R polypeptides, however, in general, the glycosylation occurring in plants is different from that produced in mammalian cells, and may result in a glycosylated product which is not suitable for human therapeutic use.

Polypeptide Production

Host cells comprising a TALL-1R polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a TALL-1R polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a TALL-1R polypeptide has been designed to be secreted from the host cells, the majority of polypeptide may be found in the cell culture medium. If however, the TALL-1R polypeptide is not secreted from the host cells, it will be present in the cytoplasm and/or the nucleus (for eukaryotic host cells) or in the cytosol (for gram-negative bacteria host cells).

For a TALL-1R polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a TALL-1R polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized TALL-1R polypeptide can then be analyzed using gel electrophoresis, immunoprecipitation, or the like. If it is desired to isolate the TALL-1R polypeptide, isolation may be accomplished using standard methods such as those described herein and in Marston et al., 1990, *Meth. Enz.,* 182:264-75.

In some cases, a TALL-1R polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b (ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a TALL-1R polypeptide, then the polypeptide will be found primarily in the supernatant after centrifugation of the cell homogenate. The polypeptide may be further isolated from the supernatant using methods such as those described herein.

The purification of a TALL-1R polypeptide from solution can be accomplished using a variety of techniques. If the polypeptide has been synthesized such that it contains a tag such as Hexahistidine (TALL-1R polypeptide/hexaHis) or other small peptide such as FLAG (Eastman Kodak Co., New Haven, Conn.) or myc (Invitrogen) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of TALL-1R polypeptide/polyHis. See, e.g., *Current Protocols in Molecular Biology* § 10.11.8 (Ausubel et al, eds., Green Publishers Inc. and Wiley and Sons 1993).

Additionally, TALL-1R polypeptides may be purified through the use of a monoclonal antibody that is capable of specifically recognizing and binding to a TALL-1R polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

TALL-1R polypeptides may also be prepared by chemical synthesis methods (such as solid phase peptide synthesis) using techniques known in the art such as those set forth by Merrifield et al, 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized TALL-1R polypeptides may be oxidized using methods set forth in these references to form disulfide bridges. Chemically synthesized TALL-1R polypeptides are expected to have comparable biological activity to the corresponding TALL-1R polypeptides produced recombinantly or purified from natural sources, and thus may be used interchangeably with a recombinant or natural TALL-1R polypeptide.

Another means of obtaining TALL-1R polypeptide is via purification from biological samples such as source tissues and/or fluids in which the TALL-1R polypeptide is naturally found. Such purification can be conducted using methods for protein purification as described herein. The presence of the TALL-1R polypeptide during purification may be monitored, for example, using an antibody prepared against recombinantly produced TALL-1R polypeptide or peptide fragments thereof.

A number of additional methods for producing nucleic acids and polypeptides are known in the art, and the methods can be used to produce polypeptides having specificity for TALL-1R polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in International Pub. No. WO99/15650, filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell that is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive TALL-1R polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more TALL-1R polypeptides. Suitable selective binding agents include, but are not limited to, antibodies and derivatives thereof, polypeptides, and small molecules. Suitable selective binding agents may be prepared using methods known in the art. An exemplary TALL-1R polypeptide selective binding agent of the present invention is capable of binding a certain portion of the TALL-1R polypeptide thereby inhibiting the binding of the polypeptide to a TALL-1R polypeptide receptor.

Selective binding agents such as antibodies and antibody fragments that bind TALL-1R polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the TALL-1R polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a TALL-1R polypeptide generally are produced in animals (e.g., rabbits or mice) by means of multiple subcutaneous or intraperitoneal injections of TALL-1R polypeptide and an adjuvant. It may be useful to conjugate a TALL-1R polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-TALL-1R antibody titer.

Monoclonal antibodies directed toward TALL-1R polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with TALL-1R polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al, 1986, *Nature* 321:522-25; Riechmann et al, 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind TALL-1R polypeptides. Using transgenic animals (e.g., mice) that are capable of producing a repertoire of human antibodies in the absence of endogenous immunoglobulin production such antibodies are produced by immunization with a TALL-1R polypeptide antigen (i.e., having at least 6 contiguous amino acids), optionally conjugated to a carrier. See, e.g., Jakobovits et al, 1993, *Proc. Natl. Acad. Sci.* 90:2551-55; Jakobovits et al, 1993, *Nature* 362:255-58; Bruggermann et al, 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is animals having less than the full complement of modifications, are then cross-bred to obtain an animal having all of the desired immune system modifications. When administered an immunogen, these transgenic animals produce antibodies with human (rather than, e.g., murine) amino acid sequences, including variable regions that are immunospecific for these antigens. See International Pub. Nos. WO 96/33735 and WO 94/02602. Additional methods are described in U.S. Pat. No. 5,545,807, International Pub. Nos. WO 91/10741 and WO 90/04036, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in International Pub. No. WO 99/10494, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-TALL-1R antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of TALL-1R polypeptides. The antibodies will bind TALL-1R polypeptides with an affinity that is appropriate for the assay method being employed.

For diagnostic applications, in certain embodiments, anti-TALL-1R antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a TALL-1R polypeptide, or an immunologically reactive portion thereof) to compete with the test sample analyte (an TALL-1R polypeptide) for binding with a limited amount of anti-TALL-1R antibody. The amount of a TALL-1R polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-TALL-1R antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a TALL-1R polypeptide. In one embodiment, antagonist antibodies of the invention are antibodies or binding fragments thereof which are capable of specifically binding to a TALL-1R polypeptide and which are capable of inhibiting or eliminating the functional activity of a TALL-1R polypeptide in vivo or in vitro. In preferred embodiments, the selective binding agent, e.g., an antagonist antibody, will inhibit the functional activity of a TALL-1R polypeptide by at least about 50%, and preferably by at least about 80%. In another embodiment, the selective binding agent may be an anti-TALL-1R polypeptide antibody that is capable of interacting with a TALL-1R polypeptide binding partner (a ligand or receptor) thereby inhibiting or eliminating TALL-1R polypeptide activity in vitro or in vivo. Selective binding agents, including agonist and antagonist anti-TALL-1R polypeptide antibodies, are identified by screening assays that are well known in the art. The invention also relates to a kit comprising TALL-1R selective binding agents (such as antibodies) and other reagents useful for detecting TALL-1R polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the TALL-1R molecules of the invention, including, but not limited to: the identification and validation of TALL-1R disease-related genes as targets for therapeutics; molecular toxicology of related TALL-1R molecules and inhibitors thereof; stratification of populations and generation of surrogate markers for clinical trials; and enhancing related TALL-1R polypeptide small molecule drug discovery by aiding in the identification of selective compounds in high throughput screens.

Chemical Derivatives

Chemically modified derivatives of TALL-1R polypeptides may be prepared by one skilled in the art, given the disclosures described herein. TALL-1R polypeptide derivatives are modified in a manner that is different—either in the type or location of the molecules naturally attached to the polypeptide. Derivatives may include molecules formed by the deletion of one or more naturally—attached chemical groups. The polypeptide comprising the amino acid sequence of any of SEQ ID NO: 2, SEQ ID NO: 4, SEQ ID NO: 6, SEQ ID NO: 7, or SEQ ID NO: 14, or other TALL-1R polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone)polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that may be used to prepare covalently attached TALL-1R polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of any of SEQ ID NO: 2, SEQ ID NO: 4, SEQ ID NO: 6, SEQ ID NO: 7, or SEQ ID NO: 14, or other TALL-1R polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the TALL-1R polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, TALL-1R polypeptides may be chemically coupled to biotin. The biotin/TALL-1R polypeptide molecules are then allowed to bind to avidin, resulting in tetravalent avidin/biotin/TALL-1R polypeptide molecules. TALL-1R polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present TALL-1R polypeptide derivatives include those described herein for TALL-1R polypeptides. However, the TALL-1R polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native TALL-1R polypeptide have been disrupted (i.e., "knocked out") such that the level of expression of TALL-1R polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a TALL-1R gene for that animal or a heterologous TALL-1R gene is over-expressed by the animal, thereby creating a "transgenic" animal. Such transgenic animals may be prepared using well known methods such as those described in U.S. Pat. No. 5,489,743 and International Pub. No. WO 94/28122.

The present invention further includes non-human animals in which the promoter for one or more of the TALL-1R polypeptides of the present invention is either activated or inactivated (e.g., by using homologous recombination methods) to alter the level of expression of one or more of the native TALL-1R polypeptides.

These non-human animals may be used for drug candidate screening. In such screening, the impact of a drug candidate on the animal may be measured. For example, drug candidates may decrease or increase the expression of the TALL-1R gene. In certain embodiments, the amount of TALL-1R polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of TALL-1 R Polypeptide Activity

In some situations, it may be desirable to identify molecules that are modulators, i.e., agonists or antagonists, of the activity of TALL-1R polypeptide. Natural or synthetic molecules that modulate TALL-1R polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a TALL-1R polypeptide. Most commonly, a test molecule will interact directly with a TALL-1 R polypeptide. However, it is also contemplated that a test molecule may also modulate TALL-1R polypeptide activity indirectly, such as by affecting TALL-1R gene expression, or by binding to a TALL-1R polypeptide binding partner (e.g., receptor or ligand). In one embodiment, a test molecule will bind to a TALL-1R polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with TALL-1R polypeptides are encompassed by the present invention. In certain embodiments, a TALL-1R polypeptide is incubated with a test molecule under conditions that permit the interaction of the test molecule with a TALL-1R polypeptide, and the extent of the interaction is measured. The test molecule can be screened in a substantially purified form or in a crude mixture.

In certain embodiments, a TALL-1R polypeptide agonist or antagonist may be a protein, peptide, carbohydrate, lipid, or small molecular weight molecule that interacts with TALL-1R polypeptide to regulate its activity. Molecules which regulate TALL-1R polypeptide expression include nucleic acids which are complementary to nucleic acids encoding a TALL-1R polypeptide, or are complementary to nucleic acids sequences which direct or control the expression of TALL-1R polypeptide, and which act as anti-sense regulators of expression.

Once a test molecule has been identified as interacting with a TALL-1R polypeptide, the molecule may be further evaluated for its ability to increase or decrease TALL-1R polypeptide activity. The measurement of the interaction of a test molecule with TALL-1R polypeptide may be carried out in several formats, including cell-based binding assays, membrane binding assays, solution-phase assays, and immunoassays. In general, a test molecule is incubated with a TALL-1R polypeptide for a specified period of time, and TALL-1R polypeptide activity is determined by one or more assays for measuring biological activity.

The interaction of test molecules with TALL-1R polypeptides may also be assayed directly using polyclonal or monoclonal antibodies in an immunoassay. Alternatively, modified forms of TALL-1R polypeptides containing epitope tags as described herein may be used in solution and immunoassays.

In the event that TALL-1R polypeptides display biological activity through an interaction with a binding partner (e.g., a receptor or a ligand), a variety of in vitro assays may be used to measure the binding of a TALL-1R polypeptide to the corresponding binding partner (such as a selective binding agent, receptor, or ligand). These assays may be used to screen test molecules for their ability to increase or decrease the rate and/or the extent of binding of a TALL-1R polypeptide to its binding partner. In one assay, a TALL-1R polypeptide is immobilized in the wells of a microtiter plate. Radiolabeled TALL-1R polypeptide binding partner (for example, iodinated TALL-1R polypeptide binding partner) and a test molecule can then be added either one at a time (in either order) or simultaneously to the wells. After incubation, the wells can be washed and counted for radioactivity, using a scintillation counter, to determine the extent to which the binding partner bound to the TALL-1R polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing TALL-1R polypeptide binding partner to the microtiter plate wells, incubating with the test molecule and radiolabeled TALL-1R polypeptide, and determining the extent of TALL-1R polypeptide binding. See, e.g., *Current Protocols in Molecular Biology*, chap. 18 (Ausubel et al., eds., Green Publishers Inc. and Wiley and Sons 1995).

As an alternative to radiolabeling, a TALL-1R polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a TALL-1R polypeptide or to a TALL-1R polypeptide binding partner, and which is conjugated to biotin, may also be used for purposes of detection following incubation of the complex with enzyme-linked streptavidin linked to AP or HRP.

A TALL-1R polypeptide or a TALL-1R polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a TALL-1R polypeptide and its binding partner can be assessed using the methods described herein. Alternatively, the substrate-protein complex can be immobilized in a column with the test molecule and complementary protein passing through the column. The formation of a complex between a TALL-1R polypeptide and its binding partner can then be assessed using any of the techniques described herein (e.g., radiolabelling or antibody binding).

Another in vitro assay that is useful for identifying a test molecule which increases or decreases the formation of a complex between a TALL-1R polypeptide binding protein and a TALL-1R polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either TALL-1R polypeptide or a TALL-1R polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a TALL-1R polypeptide and a TALL-1R polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a TALL-1R polypeptide and TALL-1R polypeptide binding partner. The assays may be automated to screen compounds generated in phage display, synthetic peptide, and chemical synthesis libraries.

Compounds which increase or decrease the formation of a complex between a TALL-1R polypeptide and a TALL-1R polypeptide binding partner may also be screened in cell culture using cells and cell lines expressing either TALL-1R polypeptide or TALL-1R polypeptide binding partner. Cells and cell lines may be obtained from any mammal, but preferably will be from human or other primate, canine, or rodent sources. The binding of a TALL-1R polypeptide to cells expressing TALL-1R polypeptide binding partner at the surface is evaluated in the presence or absence of test molecules, and the extent of binding may be determined by, for example, flow cytometry using a biotinylated antibody to a TALL-1R polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the TALL-1R gene. In certain embodiments, the amount of TALL-1R polypeptide or a TALL-1R polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 8) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 9), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a TALL-1R antagonist (such as an anti-TALL-1R selective binding agent, small molecule, soluble receptor, or antisense oligonucleotide) can be administered intracellularly to inhibit the activity of a TALL-1R molecule. As used herein, the term "TALL-1R molecule" refers to both TALL-1R nucleic acid molecules and TALL-1R polypeptides as defined herein. Where desired, the TALL-1R protein itself may also be internally administered to a cell using these procedures. See also, Straus, 1999, *Science* 285:1466-67.

Cell Source Identification using TALL-1R Polypeptide

In accordance with certain embodiments of the invention, it may be useful to be able to determine the source of a certain cell type associated with a TALL-1R polypeptide. For example, it may be useful to determine the origin of a disease or pathological condition as an aid in selecting an appropriate therapy. In certain embodiments, nucleic acids encoding a TALL-1R polypeptide can be used as a probe to identify cells described herein by screening the nucleic acids of the cells with such a probe. In other embodiments, one may use anti-TALL-1R polypeptide antibodies to test for the presence of TALL-1R polypeptide in cells, and thus, determine if such cells are of the types described herein.

TALL-1R Polypeptide Compositions and Administration

Therapeutic compositions are within the scope of the present invention. Such TALL-1R polypeptide pharmaceutical compositions may comprise a therapeutically effective amount of a TALL-1R polypeptide or a TALL-1R nucleic acid molecule in admixture with a pharmaceutically or physiologically acceptable formulation agent selected for suitability with the mode of administration. Pharmaceutical compositions may comprise a therapeutically effective amount of one or more TALL-1R polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the TALL-1R molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, TALL-1R polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the TALL-1R polypeptide product may be formulated as a lyophilizate using appropriate excipients such as sucrose.

The TALL-1R polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired TALL-1R molecule in a pharmaceutically acceptable vehicle. A particularly suitable vehicle for parenteral injection is sterile distilled water in which a TALL-1R molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, TALL-1R polypeptide may be formulated as a dry powder for inhalation. TALL-1R polypeptide or nucleic acid molecule inhalation solutions may also be formulated with a propellant for aerosol delivery. In yet another embodiment, solutions may be nebulized. Pulmonary administration is further described in Interntaional Pub. No. WO 94/20069, which describes the pulmonary delivery of chemically modified proteins.

It is also contemplated that certain formulations may be administered orally. In one embodiment of the present invention, TALL-1R polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the TALL-1R polypeptide. Diluents, flavorings, low melting point waxes, vegetable oils, lubricants, suspending agents, tablet disintegrating agents, and binders may also be employed.

Another pharmaceutical composition may involve an effective quantity of TALL-1R polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional TALL-1R polypeptide pharmaceutical compositions will be evident to those skilled in the art, including formulations involving TALL-1R polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., International Pub. No. WO 93/15722, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The TALL-1R pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a TALL-1R pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the TALL-1R molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the TALL-1R molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use TALL-1R polypeptide pharmaceutical compositions in an ex vivo manner. In such instances, cells, tissues, or organs that have been removed from the patient are exposed to TALL-1R polypeptide pharmaceutical compositions after which the cells, tissues, or organs are subsequently implanted back into the patient.

In other cases, a TALL-1R polypeptide can be delivered by implanting certain cells that have been genetically engineered, using methods such as those described herein, to express and secrete the TALL-1R polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more TALL-1R polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent TALL-1R gene, or an under-expressed gene, and thereby produce a cell which expresses therapeutically efficacious amounts of TALL-1R polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; and International Pub. Nos. WO 91/09955 and WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a TALL-1R polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired TALL-1R polypeptide. The control element controls a portion of the DNA present in the host cell genome. Thus, the expression of the desired TALL-1R polypeptide may be achieved not by transfection of DNA that encodes the TALL-1R gene itself, but rather by the use of targeting DNA (containing regions of homology with the endogenous gene of interest) coupled with DNA regulatory segments that provide the endogenous gene sequence with recognizable signals for transcription of a TALL-1R gene.

In an exemplary method, the expression of a desired targeted gene in a cell (i.e., a desired endogenous cellular gene) is altered via homologous recombination into the cellular genome at a preselected site, by the introduction of DNA that includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, TALL-1R polypeptide production from a cell's endogenous TALL-1R gene involves first using homologous recombination to place a recombination sequence from a site-specific recombination system (e.g., Cre/loxP, FLP/FRT) (Sauer, 1994, *Curr. Opin. Biotechnol.,* 5:521-27; Sauer, 1993, *Methods Enzymol.,* 225:890-900) upstream of (i.e., 5' to) the cell's endogenous genomic TALL-1R polypeptide coding region. A plasmid containing a recombination site homologous to the site that was placed just upstream of the genomic TALL-1R polypeptide coding region is introduced into the modified cell line along with the appropriate recombinase enzyme. This recombinase causes the plasmid to integrate, via the plasmid's recombination site, into the recombination site located just upstream of the genomic TALL-1R polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased TALL-1R polypeptide production from the cell's endogenous TALL-1R gene.

A further method to use the cell line in which the site specific recombination sequence had been placed just upstream of the cell's endogenous genomic TALL-1R polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.,* 5:521-27; Sauer, 1993, *Methods Enzymol.,* 225:890-900) that would create a new or modified transcriptional unit resulting in de novo or increased TALL-1R polypeptide production from the cell's endogenous TALL-1R gene.

An additional approach for increasing, or causing, the expression of TALL-1R polypeptide from a cell's endogenous TALL-1R gene involves increasing, or causing, the expression of a gene or genes (e.g., transcription factors) and/or decreasing the expression of a gene or genes (e.g., transcriptional repressors) in a manner which results in de novo or increased TALL-1R polypeptide production from the cell's endogenous TALL-1R gene. This method includes the introduction of a non-naturally occurring polypeptide (e.g., a polypeptide comprising a site specific DNA binding domain fused to a transcriptional factor domain) into the cell such that de novo or increased TALL-1R polypeptide production from the cell's endogenous TALL-1R gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of TALL-1R polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a TALL-1R polypeptide, which nucleotides may be used as targeting sequences.

TALL-1R polypeptide cell therapy, e.g., the implantation of cells producing TALL-1R polypeptides, is also contemplated. This embodiment involves implanting cells capable of synthesizing and secreting a biologically active form of TALL-1R polypeptide. Such TALL-1R polypeptide-producing cells can be cells that are natural producers of TALL-1R polypeptides or may be recombinant cells whose ability to produce TALL-1R polypeptides has been augmented by transformation with a gene encoding the desired TALL-1R polypeptide or with a gene augmenting the expression of TALL-1R polypeptide. Such a modification may be accomplished by means of a vector suitable for delivering the gene as well as promoting its expression and secretion. In order to minimize a potential immunological reaction in patients being administered a TALL-1R polypeptide, as may occur with the administration of a polypeptide of a foreign species, it is preferred that the natural cells producing TALL-1R polypeptide be of human origin and produce human TALL-1R polypeptide. Likewise, it is preferred that the recombinant cells producing TALL-1R polypeptide be transformed with an expression vector containing a gene encoding a human TALL-1R polypeptide.

Implanted cells may be encapsulated to avoid the infiltration of surrounding tissue. Human or non-human animal cells may be implanted in patients in biocompatible, semipermeable polymeric enclosures or membranes that allow the release of TALL-1R polypeptide, but that prevent the destruction of the cells by the patient's immune system or by other detrimental factors from the surrounding tissue. Alternatively, the patient's own cells, transformed to produce TALL-1R polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (International Pub. No. WO 95/05452 and International Pub. No. WO 95/05452) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in International Pub. No. WO 91/10425 (Aebischer et al.). See also, International Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of TALL-1R polypeptides is also envisioned. One example of a gene therapy technique is to use the TALL-1R gene (either genomic DNA, cDNA, and/or synthetic DNA) encoding a TALL-1R polypeptide that may be operably linked to a constitutive or inducible promoter to form a "gene therapy DNA construct." The promoter may be homologous or heterologous to the endogenous TALL-1R gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the TALL-1R gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see International Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and International Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and International Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding TALL-1R polypeptide into cells via local injection of a TALL-1R nucleic acid molecule or by other appropriate viral or non-viral delivery vectors. Hefti 1994, *Neurobiology* 25:1418-35. For example, a nucleic acid molecule encoding a TALL-1R polypeptide may be contained in an adeno-associated virus (AAV) vector for delivery to the targeted cells (see, e.g., International Pub. Nos. WO 95/34670 and WO 95/34670). The recombinant AAV genome typically contains AAV inverted terminal repeats flanking a DNA sequence encoding a TALL-1R polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and International Pub. No. WO 96/40958 (involving nuclear ligands).

It is also contemplated that TALL-1R gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous TALL-1R polypeptide expression in a cell via gene therapy is to insert one or more enhancer elements into the TALL-1R polypeptide promoter, where the enhancer elements can serve to increase transcriptional activity of the TALL-1R gene. The enhancer elements used will be selected based on the tissue in which one desires to activate the gene—enhancer elements known to confer promoter activation in that tissue will be selected. For example, if a gene encoding a TALL-1R polypeptide is to be "turned on" in T-cells, the lck promoter enhancer element may be used. Here, the functional portion of the transcriptional element to be added may be inserted into a fragment of DNA containing the TALL-1R polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease TALL-1R polypeptide expression by modifying the nucleotide sequence of the endogenous promoter. Such modification is typically accomplished via homologous recombination methods. For example, a DNA molecule containing all or a portion of the promoter of the TALL-1R gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding TALL-1R gene. The deletion of the TATA box or the transcription activator binding site in the promoter may be accomplished by generating a DNA construct comprising all or the relevant portion of the TALL-1R polypeptide promoter (from the same or a related species as the TALL-1R gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic uses

TALL-1R nucleic acid molecules, polypeptides, and agonists and antagonists thereof can be used to treat, diagnose, ameliorate, or prevent a number of diseases, disorders, or conditions, including those recited herein.

TALL-1R polypeptide agonists and antagonists include those molecules which regulate TALL-1R polypeptide activity and either increase or decrease at least one activity of the mature form of the TALL-1R polypeptide. Agonists or antagonists may be co-factors, such as a protein, peptide, carbohydrate, lipid, or small molecular weight molecule, which interact with TALL-1R polypeptide and thereby regulate its activity. Potential polypeptide agonists or antagonists include antibodies that react with either soluble or membrane-bound forms of TALL-1R polypeptides that comprise part or all of the extracellular domains of the said proteins. Molecules that regulate TALL-1R polypeptide expression typically include nucleic acids encoding TALL-1R polypeptide that can act as anti-sense regulators of expression.

The TALL-1R nucleic acid molecules, polypeptides, and agonists and antagonists thereof of the present invention are useful for the same purposes for which other members of the TNFR family of polypeptides are known to be useful. For example, the TALL-1R polypeptides of the present invention may play a role in inflammatory or immune processes. Accordingly, TALL-1R nucleic acid molecules, polypeptides, and agonists and antagonists thereof may be useful in diagnosing or treating diseases and conditions associated with inflammation or immune function. Examples of such diseases and conditions include, but are not limited to, infections such as bacterial, fungal, protozoan and viral infections (especially HIV-1 or HIV-2); diarrhea; psoriasis and inflammation; allergies; respiratory allergic diseases such as asthma, allergic rhinitis, hypersensitivity lung disease, hypersensitivity pneumonitis, eosinophilic pneumonia (e.g., Loeffler's syndrome, chronic eosinophilic pneumonia, interstitial lung disease (ILD) such as idiopathic pulmonary fibrosis or ILD associated with rheumatoid arthritis, systemic lupus erythematosus, ankylosing spondylitis, systemic sclerosis, Sjogren's syndrome, polymyositis, and dermatomyositis), systemic anaphylaxis or hypersensitivity responses; drug allergy; insect sting allergy; inflammatory bowel disease such as Crohn's disease and ulcerative colitis; spondyloarthropathy; scleroderma; inflammatory dermatosis such as dermatitis, eczema, atopic dermatitis, allergic contact dermatitis, urticaria, vasculitis (e.g., necrotizing, cutaneous, or hypersensitivity vasculitis); inflammatory joint disease; inflammatory conditions resulting from strain, sprain, cartilage damage, trauma, orthopedic surgery, infection or other disease processes; eosinphilic myositis and eosinophilic fasciitis; autoimmune diseases such as rheumatoid arthritis, psoriatic arthritis, inflammatory arthritis, osteoarthritis, multiple sclerosis, systemic lupus erythematosus, myasthenia gravis, diabetes mellitus, juvenile onset diabetes, glomerulonephritis, autoimmune thyroiditis, immune thrombocytopenic purpura (ITP), and Behcet's disease; graft rejection, including allograft rejection or graft-versus-host disease; cancers with leukocyte infiltration of the skin or organs; reperfusion injury, atherosclerosis; certain hematologic malignancies; septic shock and endotoxic shock. Modulators of TALL-1R polypeptide function also may be useful in treating: immunosuppression (e.g., in AIDS patients or individuals undergoing radiation therapy), chemotherapy, therapy for autoimmune disease or other drug therapy, and immunosuppression due to congenital deficiency in receptor function or other causes, and infectious diseases such as parasitic diseases, including helminth infections, such as nematodes (round worms). Other diseases and conditions associated with inflammation or immune function are encompassed within the scope of the invention.

Since TALL-1 binding to human peripheral blood lymphocytes and to the human B-cell line, BJAB, appears to be mediated by TALL-1R polypeptides, TALL-1R nucleic acid molecules, polypeptides, and agonists and antagonists thereof may be useful in diagnosing or treating B-cell neoplasms. Examples of such diseases and conditions include, but are not limited to, B-cell Non-Hodgkin's lymphomas, such as small lymphocytic lymphoma, lymphoplasmacytoid lymphoma, mantle cell lymphoma, follicular lymphoma, mucosa-associated lymphoid tissue lymphoma, diffuse large cell lymphoma, and Burkitt's lymphoma; precursor B-lymphoblastic leukemia; and B-cell chronic lymphoblastic leukemia, and multiple myeloma. Other B-cell neoplasms are encompassed within the scope of the invention.

Agonists or antagonists of TALL-1R polypeptide function may be used (simultaneously or sequentially) in combination with one or more cytokines, growth factors, antibiotics, anti-inflammatories, and/or chemotherapeutic agents as is appropriate for the condition being treated.

Other diseases or disorders caused by or mediated by undesirable levels of TALL-1R polypeptides are encompassed within the scope of the invention. Undesirable levels include excessive levels of TALL-1R polypeptides and sub-normal levels of TALL-1R polypeptides.

Uses of TALL-1R Nucleic Acids and Polypeptides

Nucleic acid molecules of the invention (including those that do not themselves encode biologically active polypeptides) may be used to map the locations of the TALL-1R gene and related genes on chromosomes. Mapping may be done by techniques known in the art, such as PCR amplification and in situ hybridization.

TALL-1R nucleic acid molecules (including those that do not themselves encode biologically active polypeptides), may be useful as hybridization probes in diagnostic assays to test, either qualitatively or quantitatively, for the presence of a TALL-1R nucleic acid molecule in mammalian tissue or bodily fluid samples.

Other methods may also be employed where it is desirable to inhibit the activity of one or more TALL-1R polypeptides. Such inhibition may be effected by nucleic acid molecules that are complementary to and hybridize to expression control sequences (triple helix formation) or to TALL-1R mRNA. For example, antisense DNA or RNA molecules, which have a sequence that is complementary to at least a portion of a TALL-1R gene can be introduced into the cell. Anti-sense probes may be designed by available techniques using the sequence of the TALL-1R gene disclosed herein. Typically, each such antisense molecule will be complementary to the start site (5' end) of each selected TALL-1R gene. When the antisense molecule then hybridizes to the corresponding TALL-1R mRNA, translation of this mRNA is prevented or reduced. Anti-sense inhibitors provide information relating to the decrease or absence of a TALL-1R polypeptide in a cell or organism.

Alternatively, gene therapy may be employed to create a dominant-negative inhibitor of one or more TALL-1R polypeptides. In this situation, the DNA encoding a mutant polypeptide of each selected TALL-1R polypeptide can be prepared and introduced into the cells of a patient using either viral or non-viral methods as described herein. Each such mutant is typically designed to compete with endogenous polypeptide in its biological role.

In addition, a TALL-1R polypeptide, whether biologically active or not, may be used as an immunogen, that is, the polypeptide contains at least one epitope to which antibodies may be raised. Selective binding agents that bind to a TALL-1R polypeptide (as described herein) may be used for in vivo and in vitro diagnostic purposes, including, but not limited to, use in labeled form to detect the presence of TALL-1R polypeptide in a body fluid or cell sample. The antibodies may also be used to prevent, treat, or diagnose a number of diseases and disorders, including those recited herein. The antibodies may bind to a TALL-1R polypeptide so as to diminish or block at least one activity characteristic of a TALL-1R polypeptide, or may bind to a polypeptide to increase at least one activity characteristic of a TALL-1R polypeptide (including by increasing the pharmacokinetics of the TALL-1R polypeptide).

TALL-1R polypeptides can be used to clone TALL-1R ligands using an "expression cloning" strategy. Radiolabeled ($^{125}$Iodine) TALL-1R polypeptide or "affinity/activity-tagged" TALL-1R polypeptide (such as an Fc fusion or an alkaline phosphatase fusion) can be used in binding assays to identify a cell type, cell line, or tissue that expresses a TALL-1R ligand. RNA isolated from such cells or tissues can then be converted to cDNA, cloned into a mammalian expression vector, and transfected into mammalian cells (e.g., COS or 293) to create an expression library. Radiolabeled or tagged TALL-1R polypeptide can then be used as an affinity reagent to identify and isolate the subset of cells in this library expressing a TALL-1R ligand. DNA is then isolated from these cells and transfected into mammalian cells to create a secondary expression library in which the fraction of cells expressing the TALL-1R ligand would be many-fold higher than in the original library. This enrichment process can be repeated iteratively until a single recombinant clone containing the TALL-1R ligand is isolated. Isolation of TALL-1R ligands is useful for identifying or developing novel agonists and antagonists of the TALL-1R signaling pathway. Such agonists and antagonists include TALL-1R ligands, anti-TALL-1R ligand antibodies, small molecules or antisense oligonucleotides.

The TALL-1R nucleic acids of the present invention are also useful tools for isolating the corresponding chromosomal TALL-1R polypeptide genes. For example, mouse chromosomal DNA containing TALL-1R sequences can be used to construct knockout mice, thereby permitting an examination of the in vivo role for TALL-1R polypeptide. The human TALL-1R genomic DNA can be used to identify heritable tissue-degenerating diseases.

The following examples are intended for illustration purposes only, and should not be construed as limiting the scope of the invention in any way.

EXAMPLE 1

Characterization of TALL-1 Binding to Human Peripheral Blood Lymphocytes

TALL-1 binding to human peripheral blood lymphocytes was analyzed using specific monoclonal antibodies to either the transmembrane activator and calcium modulator and cyclophilin ligand interactor (TACI) and B cell maturation antigen (BCMA). Anti-TACI and anti-BCMA antibodies were isolated by immunizing eight-week-old female Lous rats by subcutaneous injection with 100 μg of either TACI-FC (Xia et al., 2000, *J. Exp. Med.*, 192:137-43) or BCMA-Fc (Yu et al., 2000, *Nat. Immunol.* 1:252-56), emulsified in RIBI adjuvant, and then immunizing the rats by subcutaneous injection with 50 μg of the same immunogen and adjuvant, three weeks later. Intravenous injection was used as a boosting method four days before fusing spleen cells isolated from the immunized rats with Y3 myeloma cells. Spleen cells were fused with myeloma cells at a ratio of 4:1 using a modified procedure of Kohler and Milstein, 1975, *Nature* 256:495-97. Hybridoma supernatants were screened by ELISA for specific binding to TACI-FC or BCMA-Fc, and then for the absence of binding to human IgG. Anti-TACI and anti-BCMA antibodies were purified on protein G columns as described in Harlow, *Antibodies: A Laboratory Manual* (Cold Spring Harbor Laboratory).

Figure 1B:
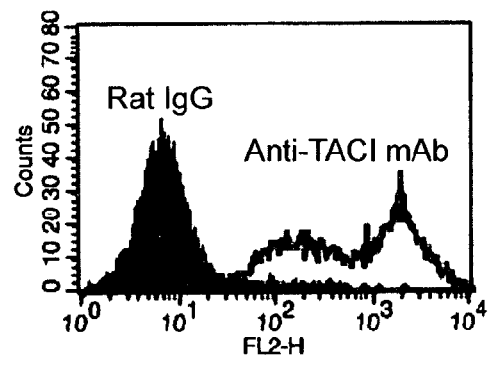
Figure 1C:
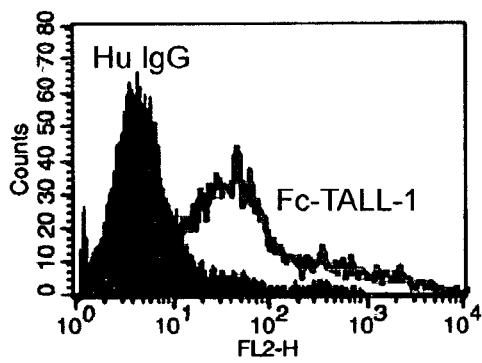
Figure 1D:
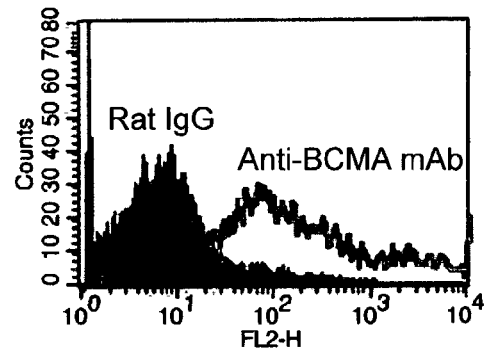

To analyze anti-TACI and anti-BCMA antibody specificity, approximately $10^6$ 293 cells were first transfected with either a TACI or BCMA expression vector, or with a vector control. Transfected cells were incubated with 1 μg/ml of anti-TACI or anti-BCMA antibody, and then with 20 μg/ml of FITC-conjugated goat anti-rat IgG. Following incubation with primary and secondary antibodies, the cells were analyzed on a Becton Dickinson FACscan. Anti-TACI antibody was found to specifically recognize 293 cells transfected with a TACI expression vector (FIG. 1B), and anti-BCMA antibody was found to specifically recognize 293 cells transfected with a BCMA expression vector (FIG. 1D).

Figure 2A:
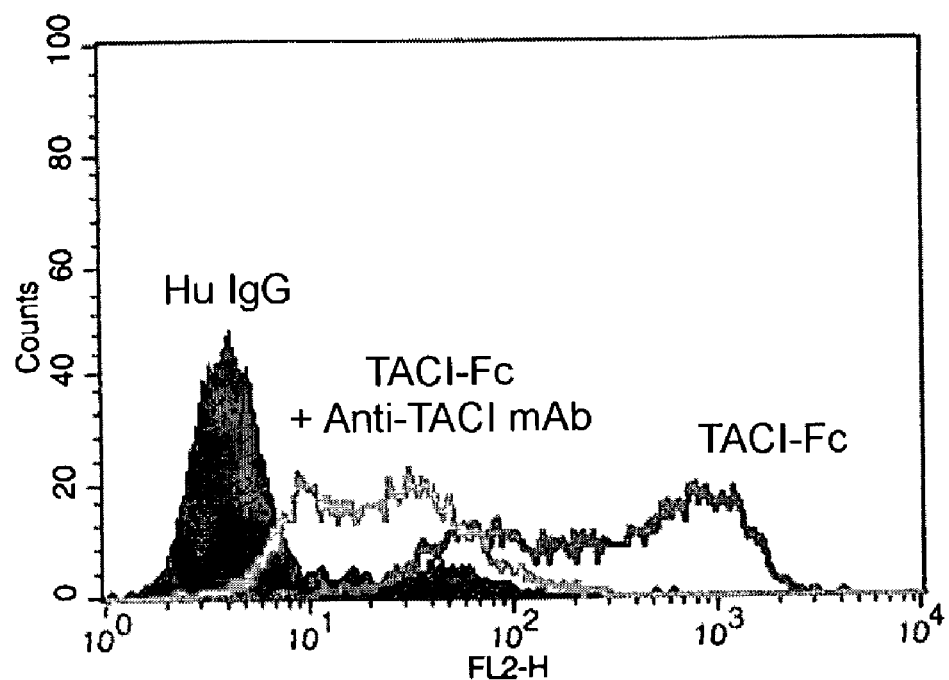
FIGS. 2A-2B show the results of FACS analysis of 293 cells transfected with TALL-1 expression vector following incubation with either TACI-Fc in the absence or presence of anti-TACI antibody (FIG. 2A) or BCMA-Fc in the absence or presence of anti-BCMA antibody (FIG. 2B)
Figure 2B:
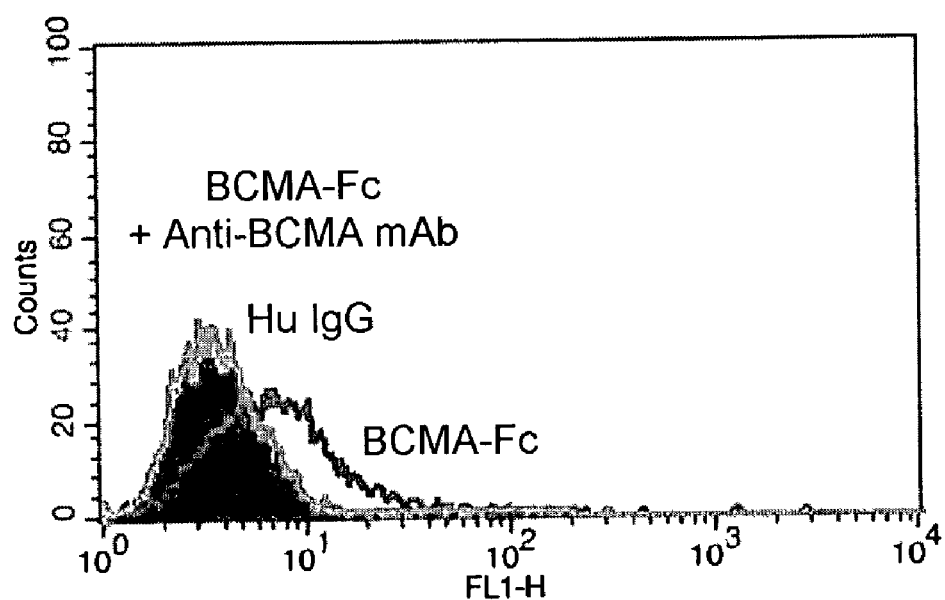

To examine anti-TACI and anti-BCMA antibody neutralizing activity, approximately $10^6$ 293 cells were first transfected with either a TALL-1 or AGP expression vector, or with a vector control. Cells transfected with a TALL-1 expression vector were incubated with 1 μg/ml of TACI-Fc in the absence or presence of 10 μg/ml of anti-TACI antibody, and then with 20 μg/ml of FITC-conjugated goat anti-rat IgG. Alternatively, cells transfected with an AGP expression vector were incubated with 1 μg/ml of BCMA-Fc in the absence or presence of 10 μg/ml of anti-BCMA antibody, and then with 20 μg/ml of FITC-conjugated goat anti-rat IgG. Following incubation with primary and secondary antibodies, the cells were analyzed on a Becton Dickinson FACscan. Anti-TACI antibody was found to completely block TACI-Fc binding to 293 cells transfected with a TALL-1 expression vector (FIG. 2A), and anti-BCMA antibody was found to completely block BCMA-Fc binding to 293 cells transfected with an AGP expression vector (FIG. 2B).

Figure 3A:
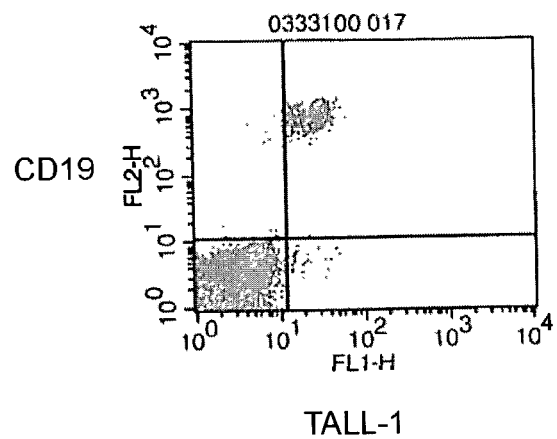
FIGS. 3A-3C show the results of FACS analysis of human peripheral blood lymphocytes following incubation with either TALL-1, anti-TACI antibody, or anti-BCMA antibody.

To analyze the level of TALL-1 binding, human peripheral blood lymphocytes (PBL) were first incubated with a PE-conjugated anti-CD19 antibody (a B cell marker) and FLAG-TALL-1, and then with a FITC-conjugated anti-FLAG antibody. Approximately 10% of the human PBL population was found to comprise CD19+ B cells. The CD19+ B cell fraction was also found to bind TALL-1, suggesting the presence of TALL-1 receptors on the human peripheral B cells (FIG. 3A).

Figure 3B:
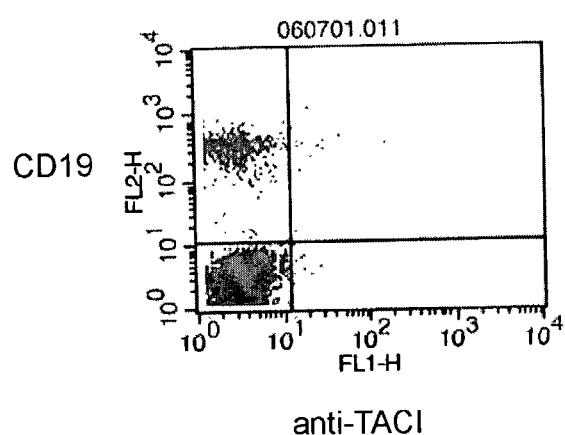
Figure 3C:
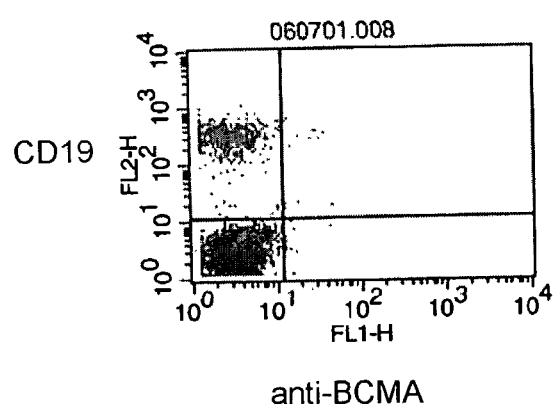

To examine TACI and BCMA expression in the human peripheral blood B cell population, human PBL were first incubated with PE-conjugated anti-CD19 antibody together with either anti-TACI or anti-BCMA, and then with a FITC-conjugated goat anti-rat antibody. No TACI or BCMA expression was detected on the human peripheral blood lymphocytes (FIGS. 3B and 3C), suggesting that the binding of TALL-1 is to some other receptor on the human PBL.

Figure 4A:
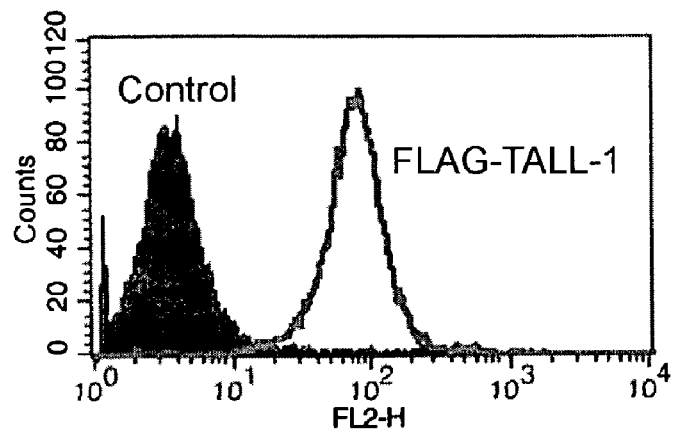
FIGS. 4A-4C show the results of FACS analysis of BJAB cells following incubation with either FLAG-TALL-1, anti-TACI antibody, or anti-BCMA antibody.
Figure 4B:
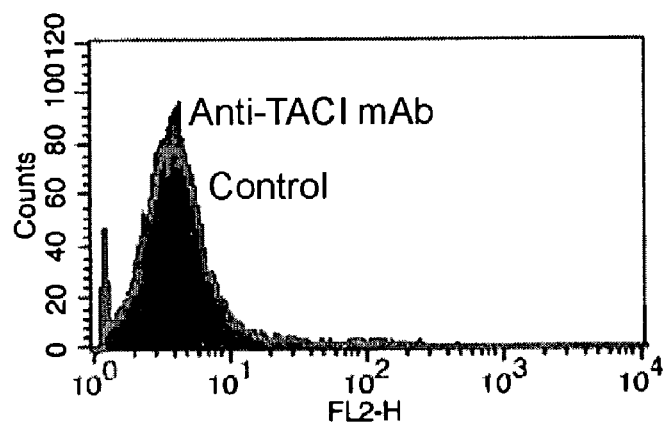
Figure 4C:
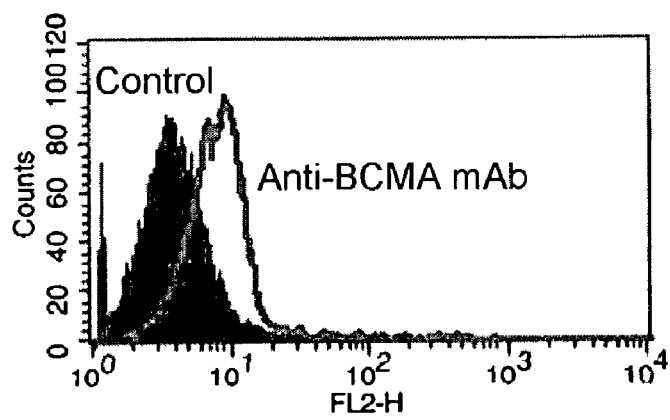

TALL-1 binding was compared with TACI or BCMA expression levels in several B lymphoma cell lines and myeloma cell lines by FACS analysis as follows. Cells were harvested from exponentially replicating cultures, pelleted by centrifugation, washed with phosphate buffered saline (PBS; Gibco) containing 1% fetal calf serum (FCS), and then resuspended at $1 \times 10^7$ cells/ml in a 96-well microtiter tissue culture plate in PBS with 1% FCS and 1 μg/ml FLAG-TALL-1. After one hour of incubation at 4° C., the cells were washed with PBS containing 1% FCS, and then incubated in PBS containing 1% FCS and 20 μg/ml FITC anti-FLAG M2 antibody (Kodak, New Haven, Conn.) for 30 minutes at 4° C. After washing with PBS, the cells were incubated in PBS containing 1% FCS and 20 μg/ml FITC-conjugated goat anti-mouse IgG (Southern Biotech Associates, Birmingham, Ala.) for 30 minutes at 4° C. After washing with PBS, the cells were analyzed using a Becton Dickinson FACscan. Similarly, cells were stained with anti-TACI or anti-BCMA antibody followed by staining with FITC-conjugated anti-rat antibody. In human B lymphoma BJAB cells, strong binding signals were detected following staining with FLAG-TALL-1 (FIG. 4A). The specificity of this binding was confirmed by the addition of 10 μg of TACI-Fc during the first incubation period. In contrast, no signal, or only a weak signal, was detected following staining with anti-TACI (FIG. 4B) or anti-BMCA (FIG. 4C) antibody. The strong binding of TALL-1 to BJAB cells suggests that TALL-1 binding might be mediated by other receptors.

EXAMPLE 2

Cloning of the Human TALL-1R Polypeptide Genes

To isolate sequences encoding human TALL-1R polypeptide, a human B lymphoma BJAB cDNA library was prepared. Exponentially growing BJAB cells were harvested, and total cellular RNA was purified by acid guanidinium thiocyanate-phenol-chloroform extraction (Chomczynski and Sacchi, 1987, *Anal. Biochem.* 162:156-59). Poly-A+ mRNA was obtained from total RNA by adsorption to, and elution from, Dynabeads Oligo $(dT)_{25}$ (Dynal Corp.; Lake Success, N.Y.), using the manufacturer's recommended procedures. A directional, oligo-dT primed cDNA library was prepared using the Superscript Plasmid System (Gibco-BRL), using the manufacturer's recommended procedures. The resulting cDNA was digested to completion with Sal I and Not I and then was fractionated by size exclusion gel chromatography. The highest molecular weight fractions were selected and ligated into the polylinker region of the expression vector, which contains a CMV promoter upstream of the multiple cloning site that directs a high level expression in eukaryotic cells. The library was introduced into competent *E. coli* (ElectroMAX DH10B; Gibco) by electroporation and transformed cells were plated on LB agar containing 100 μg/ml ampicillin. The library was then separated into pools containing approximately 100 clones/pool, and 1.0 ml cultures of each pool were grown for 16-20 hours at 37° C. Plasmid DNA from each pool was prepared using the Qiagen Qiawell 96 Ultra Plasmid Kit according to the manufacturer's recommended procedures.

The BJAB cDNA library pools were separately transfected into 293 cells, and the populations of transfected cells were then assayed for the acquisition of a cell surface TALL-1 binding protein using Multipitte™ (Sagian; Indianapolis, Ind.). First, 293 cells were plated in 96-well tissue culture plates at a density of $1.5 \times 10^4$ cells/ml in DMEM (Gibco) containing 10% FCS, and then cultured overnight. Approximately 300 ng of plasmid DNA from each of the library pools was added to 75 µl of OPTI-MEMI Reduced Serum Medium (Life Technologies; Gaithersburg, Md.), and 1 µl of DMRIE-C (Life Technologies) was added to a separate 75 µl portion of OPTI-MEMI Reduced Serum Medium. The DNA and DMRIE-C solutions were then mixed together and allowed to incubate at room temperature for 30 minutes. Following incubation, the DNA-DMRIE-C mixture was added to the plated 293 cells, and the cells were incubated for 2-5 hours at 37° C. The cells were then supplemented with an equal volume of DMEM containing 20% FCS, and were cultured for 48 hours at 37° C.

To identify those wells containing cells that express a TALL-1 binding protein, the media from the wells was removed and replaced with 100 µl of DMEM containing 2% goat serum, 5% rabbit serum (Life Technologies), and 0.1 nM europium-labeled TALL-1 protein (Xia et al., 2000), and the cells were incubated at room temperature for one hour. Following incubation, the cells were washed three times with 175 µl cold PBS, 170 µl of Enhancer Solution (EG&G Wallac; Turku, Finland) was added to the wells, and the plates were then analyzed using a Victor™ 1420 Multiplabel Counter (Wallac; Gaithersburg, Md.).

In this manner, a total of approximately 200,000 independent BJAB cDNA clones were screened (represented by 2000 transfected pools of 100 clones each), and thirteen wells, containing cells to which the europium-labeled TALL-1 protein was capable of binding, were identified. Positive signals detected in this analysis ranged from 2-10 fold. Two hundred bacterial colonies were picked from each positive pool and were cultured overnight. Plasmid DNA from each of these cultures was prepared using the Qiagen Qiawell 96 Ultra Plasmid Kit, according to the manufacturer's recommended procedures. Each plasmid prepreparation was introduced into 293 cells and the transfected cells were then examined for binding activity using europium-labeled TALL-1 as described above. Clones to which the europium-labeled TALL-1 was capable of binding were isolated from each positive pool and then subjected to sequence analysis using an Applied Biosystems 373A automated DNA sequencer and primer-driven Taq dye-terminator reactions, according to the manufacturer's recommended procedures.

An isolated clone from pool 3H6 (designated as 710) was found to possess a cDNA insert of approximately 2.4 kb. The nucleotide sequence of this cDNA insert was compared to known DNA sequences in a publicly accessible sequence database using the FASTA program (GCG; Univeristy of Wisconsin), and analyzed for the presence of long open reading frames (LORFs) using the "six-way open reading frame" application (Frames; GCG; Univeristy of Wisconsin). Sequence analysis indicated that clone 710 contained a LORF of 185 amino acid residues in the appropriate orientation (FIG. 5). Isolated clones from pools 5G10 and 9B3 (designated as 711 and 713) were found to possess a cDNA insert of approximately 4 kb. Sequence analysis indicated that these clones contained a LORF of 171 amino acids in the appropriate orientation (FIG. 6). The LORF of clones 711 and 713 differs from the LORF of clone 710 in that the former has a deletion of 14 amino acids (FIG. 8). An isolated clone from pool 2D6 (designated as 706) was found to possess a cDNA insert of approximately 2.5 kb. Sequence analysis indicated that clone 706 contained a LORF of 170 amino acids in the appropriate orientation (FIG. 7). The LORF of clone 706 differs from the LORF of clones 711 and 713 in that the former has a deletion of the alanine residue at position 46 (FIG. 8).

Figure 9A:
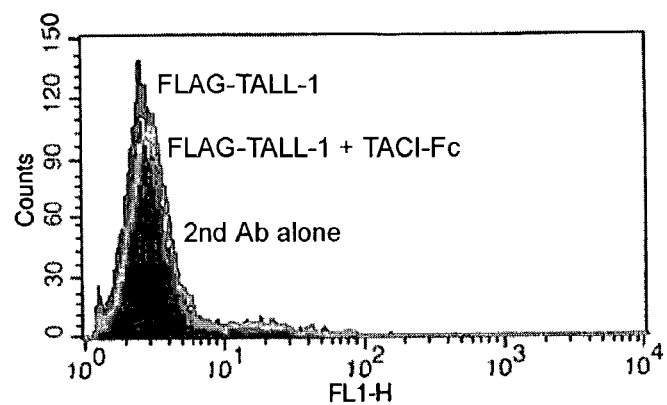
FIGS. 9A-9C shows the results of FACS analysis of 293 cells transfected with either vector control (FIG. 9A) or expression vectors containing either clone 711 (FIG. 9B) or clone 706 (FIG. 9C) cDNA sequences, following incubation with either FLAG-TALL-1 alone, or FLAG-TALL-1 and TACI-Fc, and then following further incubation with FITC-conjugated anti-FLAG antibody (2nd antibody)
Figure 9B:
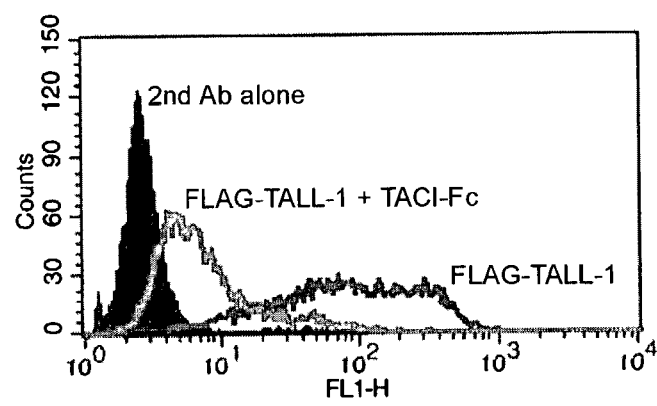
Figure 9C:
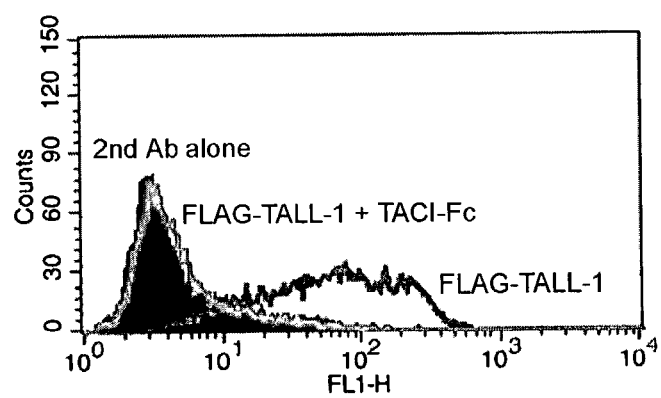

To confirm that the clones identified above contained sequences encoding TALL-1R polypeptide, approximately $10^6$ 293 cells were transfected with either a vector control or expression vectors containing clone 711 or clone 706 cDNA sequences. Transfected cells were resuspended in PBS containing 1% FCS and 1 µg/ml FLAG-TALL-1 in the absence or presence of 10 µg/ml TACI-Fc. After one hour of incubation at 4° C., the cells were washed with PBS containing 1% FCS, and then incubated in PBS containing 1% FCS and 20 µg/ml FITC anti-FLAG M2 antibody (Kodak) for 30 minutes at 4° C. After washing with PBS, the cells were incubated in PBS containing 1% FCS and 20 µg/ml FITC-conjugated goat anti-mouse IgG (Southern Biotech Associates) for 30 minutes at 4° C. After washing with PBS, the cells were analyzed using a Becton Dickinson FACscan. FLAG-TALL-1 was found to specifically bind 293 cells transfected with either the clone 711 (FIG. 9B) or clone 706 (FIG. 9C) expression vectors, but not 293 cells transfected with the vector control (FIG. 9A).

Sequence analysis indicates that the TALL-1R polypeptide contains a probable hydrophobic transmembrane domain extending from the leucine residue at position 79 of the amino acid sequence encoded by clones 710, 711, and 713 (or at position 78 for clone 706) to the valine residue at position 100 of the amino acid sequence encoded by clones 710, 711, and 713 (or at position 99 for clone 706). Such a configuration suggests that the TALL-1R polypeptide is a type III transmembrane protein, with a N-terminal extracellular domain, a transmembrane region and a C-terminal intracellular domain. A recombinant soluble form of the TALL-1R polypeptide can be created by removing nucleic acid sequences encoding the TALL-1R transmembrane region from the TALL-1R cDNA sequence. Unlike most other members of the TNFR family, the TALL-1R polypeptide contains only four cysteines within its extrallular domain.

Thompson et al, 2001 (*Science Express Reports*, 10.1126/Science.1061965) teach a nucleic acid sequence of 899 bp encoding a polypeptide of 184 amino acids that they designate as BAFF-R (a receptor for the TNF ligand, B cell activating factor). The amino acid sequence of BAFF-R shares 85% identity with the TALL-1R amino acid sequence encoded by clone 706, 86% identity with the TALL-1R amino acid sequence encoded by clone 710, and 85% identity with the TALL-1R amino acid sequence encoded by clone 711.

EXAMPLE 3

NF-κB Activation

Figure 10:
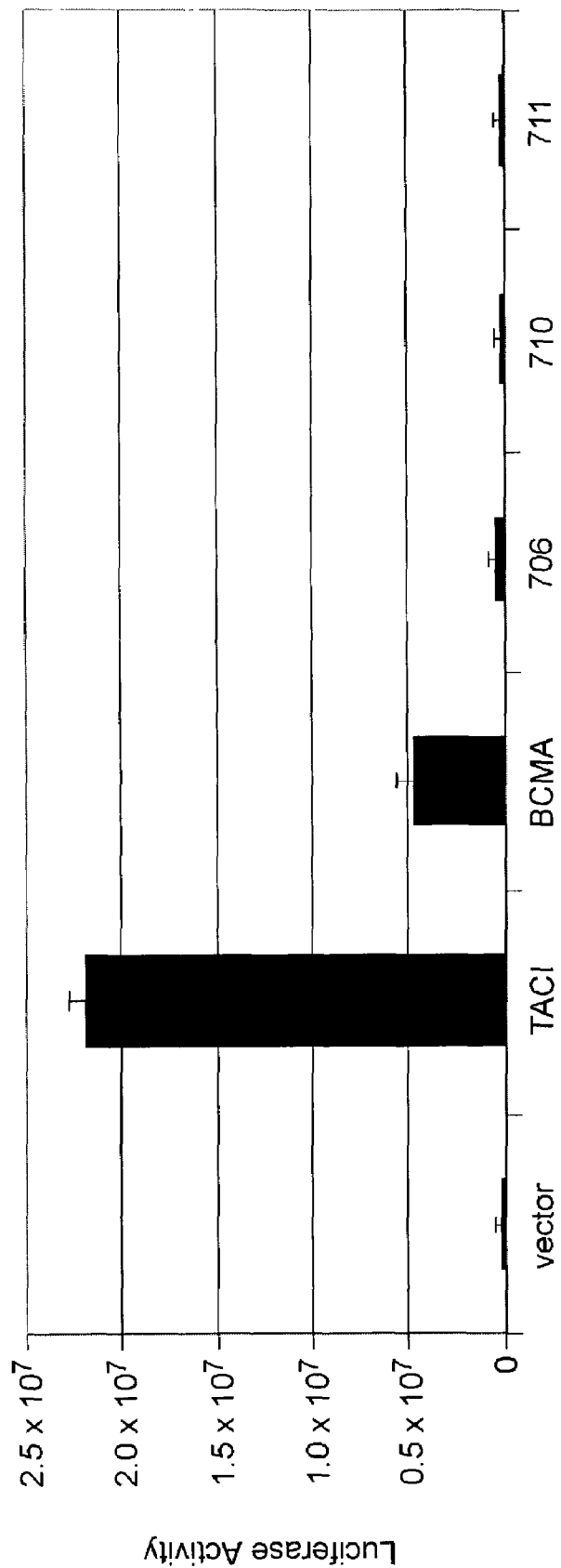
FIG. 10 shows the results of an assay for NF-κB activation in 293 cells transfected with an NF-κB-dependent luciferase reporter construct and either TACI, BCMA, clone 706, clone 710, or cone 711 expression vectors.

Most of the members of the TNFR family have been shown to induce NF-κB. The effect of TALL-1R overexpression on NF-κB activation was examined in 293 cells that were transfected with 1 µg an NF-κB-dependent luciferase reporter construct (pELAM-Luc), 0.5 µg of RSV-βgal, and 2 µg of either TACI, BCMA, clone 706, clone 710, or clone 711 expression vectors. After 24 hours, luciferase activity was measured, and this activity was normalized against β-galactosidase expression. While the overexpression of both TACI and BCMA resulted in significant activation of NF-κB, as indicated by the NF-κB dependent luciferase activity, the overexpression of clones 706, 710, and 711 failed to induce NF-κB (FIG. 10).

EXAMPLE 4

TALL-1R mRNA Expression

The expression of TALL-1R mRNA is examined by Northern blot analysis.

Multiple human tissue northern blots (Clontech) are probed with a suitable restriction fragment isolated from a human TALL-1R polypeptide cDNA clone. The probe is labeled with $^{32}$P-dCTP using standard techniques.

Northern blots are prehybridized for 2 hours at 42° C. in hybridization solution (5×SSC, 50% deionized formamide, 5× Denhardt's solution, 0.5% SDS, and 100 mg/ml denatured salmon sperm DNA) and then hybridized at 42° C. overnight in fresh hybridization solution containing 5 ng/ml of the labeled probe. Following hybridization, the filters are washed twice for 10 minutes at room temperature in 2×SSC and 0.1% SDS, and then twice for 30 minutes at 65° C. in 0.1×SSC and 0.1% SDS. The blots are then exposed to autoradiography.

The expression of TALL-1R mRNA is localized by in situ hybridization. A panel of normal embryonic and adult mouse tissues is fixed in 4% paraformaldehyde, embedded in paraffin, and sectioned at 5 μm. Sectioned tissues are permeabilized in 0.2 M HCl, digested with Proteinase K, and acetylated with triethanolamine and acetic anhydride. Sections are prehybridized for 1 hour at 60° C. in hybridization solution (300 mM NaCl, 20 mM Tris-HCl, pH 8.0, 5 mM EDTA, 1× Denhardt's solution, 0.2% SDS, 10 mM DTT, 0.25 mg/ml tRNA, 25 μg/ml polyA, 25 μg/ml polyC and 50% formamide) and then hybridized overnight at 60° C. in the same solution containing 10% dextran and $2\times10^4$ cpm/μl of a $^{33}$P-labeled antisense riboprobe complementary to the human TALL-1R gene. The riboprobe is obtained by in vitro transcription of a clone containing human TALL-1R cDNA sequences using standard techniques.

Following hybridization, sections are rinsed in hybridization solution, treated with RNaseA to digest unhybridized probe, and then washed in 0.1×SSC at 55° C. for 30 minutes. Sections are then immersed in NTB-2 emulsion (Kodak, Rochester, N.Y.), exposed for 3 weeks at 4° C., developed, and counterstained with hematoxylin and eosin. Tissue morphology and hybridization signal are simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymis, prostate, seminal vesicle, and vas deferens in the male), BAT and WAT (subcutaneous, peri-renal), bone (femur), skin, breast, and skeletal muscle.

EXAMPLE 5

Production of TALL-1R Polypeptides

A. Expression of TALL-1R Polypeptides in Bacteria

A bacterial expression construct encoding a fusion protein comprising the extracellular region of TALL-1R polypeptide and the Fc portion of human IgG1PCR was prepared by PCR. Oligonucleotides corresponding to the extracellular region of TALL-1R polypeptide were used in a first PCR amplification. The PCR product generated possessed an Nde I restriction site and methionine codon at the 5' end and an Xho I restriction site, five glycine codons, and the first six codons of the human IgG1 Fc gene at the 3' end. The PCR product generated in the first PCR amplification was used in a second PCR amplification to create the full-length TALL-1R:Fc fusion construct. The PCR product generated in the second PCR amplification was gel purified, digested with Nde I and Xho I, and cloned into the Amgen expression vector pAMG21.

The resulting expression construct, designated as pAMG21 TALL-1R:Fc, was subjected to DNA sequencing to confirm that the nucleotide sequence at the 5' and 3' ends and of the fusion junction was correct. The fusion protein encoded by pAMG21 TALL-1R:Fc was found to possess the amino acid sequence M-R-R-G-P-R-S (SEQ ID NO: 10) at the N-terminus, the amino acid sequence S-L-S-P-G-K (SEQ ID NO: 11) at the C-terminus, and the amino acid sequence V-S-L-P-L-P-G-G-G-G-G-D-K-T-H-T-C-P (SEQ ID NO: 12) at the fusion junction.

Following sequence verification, Amgen strain Ec 2596 was transformed with pAMG21 TALL-1R:Fc. Transformed cells were grown at 37° C. and then induced with homoserine lactone. Following induction, the cells were grown at 37° C. for several hours, and then harvested by centrifugation and frozen at −80° C.

Figure 11:
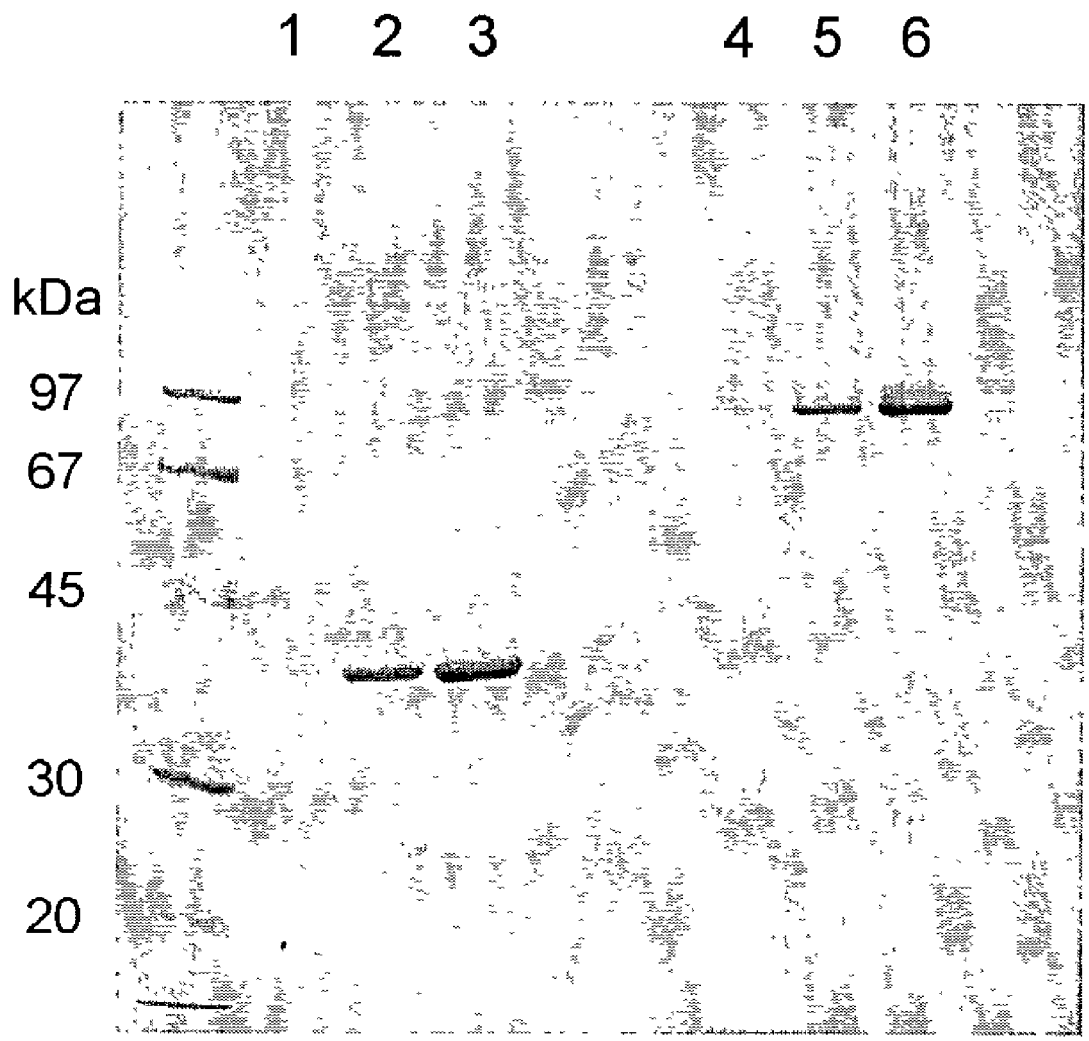
FIG. 11 shows the results of. SDS-PAGE analysis of TALL-1R:Fc polypeptide during refolding. Lanes 1-3=reduced; lanes 4-6=non-reduced; lanes 1 and 4=0.3 μg; lanes 2 and 5=1.5 μg; lanes 3 and 6=3 μg.
Figure 12:
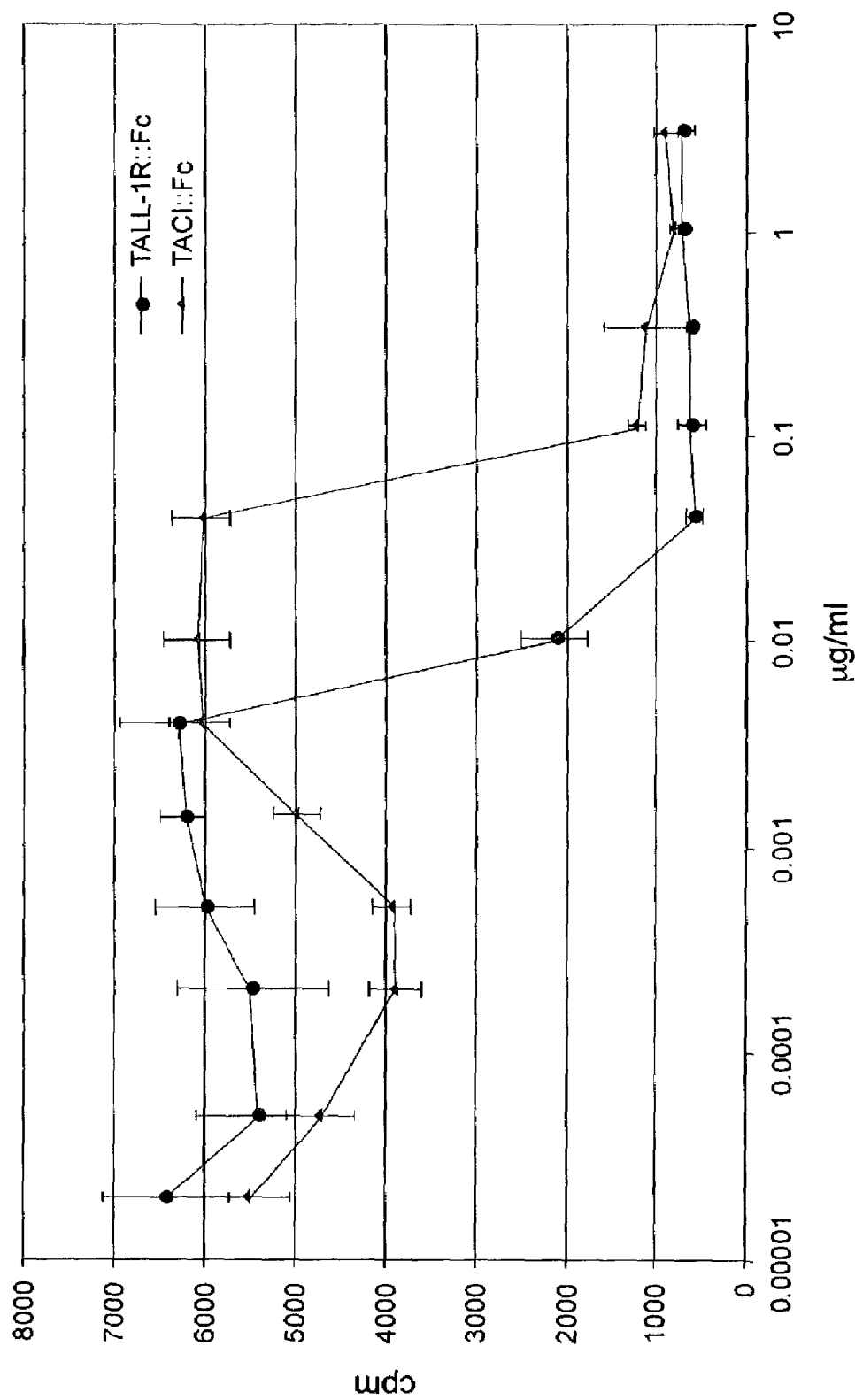
FIG. 12 shows the results of an assay for TALL-1 mediated B cell proliferation in the presence of TALL-1R:Fc and TACI:Fc fusion protein.

TALL-1R:Fc polypeptide was purified from 72 g of inclusion bodies from about 450 g of paste, and then refolded under conditions derived from a standard folding matrix (FIG. 11). The refolded material was buffer-exchanged and applied to S-ff ion exchange resin at pH 7 and then pH 5. The S-pool was then applied to Phenyl-HP HIC resin. The phenyl pool was buffer-exchanged into phosphate-buffered saline (PBS) and concentrated to 9.4 mg/ml (Endotoxin <8 EU/mg). Approximately 100 mgs of TALL-RdesA47:Fc was obtained and frozen at −80° C.

N-terminal sequencing of the purified material showed the refolded molecule started at S-L-R-G-R-D (SEQ ID NO: 13), indicating a des6 truncation of the full-length molecule. Preliminary BiaCore assay results indicated that the TALL-1R:Fc polypeptide binds TALL-1.

TALL-1R:Fc fusion protein activity was examined in a TALL-1 mediated B cell proliferation assay. B lymphocytes were isolated from the spleens of C57BL/6 mice by negative selection (MACS CD43 (Ly-48) Microbeads; Miltenyi Biotech; Auburn, Calif.). Purified ($10^5$) B cells were cultured in triplicate in 96-well flat bottom tissue culture plates in MEM containing 10% heat inactivated FCS, $5\times10^{-5}$ M 2-mercaptoethanol, 100 U/ml penicillin, 100 g/ml streptomycin, 10 ng/ml TALL-1 protein, and 2 g/ml of Goat F(ab')$_2$ anti-mouse IgM (Jackson ImmunoResearch Laboratory; West Grove, Pa.) with the indicated amount of recombinant TALL-1R:Fc fusion protein or soluble TACI:Fc fusion protein for a period of 4 days at 37° C., 5% CO$_2$. Proliferation was measured by the uptake of radioactive $^3$[H]-thymidine after an 18 hour incubation period. The TALL-1R:Fc fusion protein was more potent than TACI:Fc in the inhibition of TALL-1 mediated B cell proliferation.

B. Expression of TALL-1R Polypeptide in Mammalian Cells

PCR is used to amplify template DNA sequences encoding a TALL-1R polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen), that contains an Epstein-Barr virus origin of replication, may be used for the expression of TALL-1R polypeptides in 293-EBNA-1 cells. Amplified and gel purified PCR products are ligated into pCEP4 vector and introduced into 293-EBNA cells by lipofection. The transfected cells are selected in 100 μg/mL hygromycin and the resulting drug-resistant cultures are grown to confluence. The cells are then cultured in serum-free media for 72 hours. The conditioned media is removed and TALL-1R polypeptide expression is analyzed by SDS-PAGE.

TALL-1R polypeptide expression may be detected by silver staining. Alternatively, TALL-1R polypeptide is produced as a fusion protein with an epitope tag, such as an IgG constant domain or a FLAG epitope, which may be detected by Western blot analysis using antibodies to the peptide tag.

TALL-1R polypeptides may be excised from an SDS-polyacrylamide gel, or TALL-1R fusion proteins are purified by affinity chromatography to the epitope tag, and subjected to N-terminal amino acid sequence analysis as described herein.

C. Expression and Purification of TALL-1R Polypeptide in Mammalian Cells

TALL-1R polypeptide expression constructs are introduced into 293 EBNA or CHO cells using either a lipofection or calcium phosphate protocol.

To conduct functional studies on the TALL-1R polypeptides that are produced, large quantities of conditioned media are generated from a pool of hygromycin selected 293 EBNA clones. The cells are cultured in 500 cm Nunc Triple Flasks to 80% confluence before switching to serum free media a week prior to harvesting the media. Conditioned media is harvested and frozen at −20° C. until purification.

Conditioned media is purified by affinity chromatography as described below. The media is thawed and then passed through a 0.2 μm filter. A Protein G column is equilibrated with PBS at pH 7.0, and then loaded with the filtered media. The column is washed with PBS until the absorbance at $A_{280}$ reaches a baseline. TALL-1R polypeptide is eluted from the column with 0.1 M Glycine-HCl at pH 2.7 and immediately neutralized with 1 M Tris-HCl at pH 8.5. Fractions containing TALL-1R polypeptide are pooled, dialyzed in PBS, and stored at −70° C.

For Factor Xa cleavage of the human TALL-1R polypeptide-Fc fusion polypeptide, affinity chromatography-purified protein is dialyzed in 50 mM Tris-HCl, 100 mM NaCl, 2 mM $CaCl_2$ at pH 8.0. The restriction protease Factor Xa is added to the dialyzed protein at 1/100 (w/w) and the sample digested overnight at room temperature.

EXAMPLE 6

Production of Anti-TALL-1R Polypeptide Antibodies

Antibodies to TALL-1R polypeptides may be obtained by immunization with purified protein or with TALL-1R peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a TALL-1R antigen (such as a TALL-1R polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 μg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-TALL-1R antibody production by ELISA.

Alternative procedures for obtaining anti-TALL-1R antibodies may also be employed, such as the immunization of transgenic mice harboring human Ig loci for production of human antibodies, and the screening of synthetic antibody libraries, such as those generated by mutagenesis of an antibody variable domain.

EXAMPLE 7

Expression of TALL-1R Polypeptide in Transgenic Mice

To assess the biological activity of TALL-1R polypeptide, a construct encoding a TALL-1R polypeptide/Fc fusion protein under the control of a liver specific ApoE promoter is prepared. The delivery of this construct is expected to cause pathological changes that are informative as to the function of TALL-1R polypeptide. Similarly, a construct containing the full-length TALL-1R polypeptide under the control of the beta actin promoter is prepared. The delivery of this construct is expected to result in ubiquitous expression.

To generate these constructs, PCR is used to amplify template DNA sequences encoding a TALL-1R polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified TALL-1R polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The TALL-1R polypeptide expression vector is purified through two rounds of CsCl density gradient centrifugation, cleaved with a suitable restriction enzyme, and the linearized fragment containing the TALL-1R polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (International Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScript™ Preamplification System (Gibco-BRL) as follows. A suitable primer, located in the expression vector sequence and 3' to the TALL-1R polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for TALL-1R polypeptide.

EXAMPLE 8

Biological Activity of TALL-1R Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B-cell and T-cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1 \times 10^6$ cells from each tissue are then incubated for 10 minutes with 0.5 µg CD16/32(FcγIII/II) Fc block in a 20 µL volume. Samples are then stained for 30 minutes at 2-8° C. in a 100 µL volume of PBS (lacking $Ca^+$ and $Mg^+$), 0.1% bovine serum albumin, and 0.01% sodium azide with 0.5 µg antibody of FITC or PE-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated nucleic acid molecule comprising:
   (a) the nucleotide sequence as set forth in any of SEQ ID NO: 1, SEQ ID NO: 3, or SEQ ID NO: 5;
   (b) a nucleotide sequence encoding the polypeptide as set forth in any of SEQ ID NO: 2, SEQ ID NO: 4, SEQ ID NO: 6, SEQ ID NO: 7, or SEQ ID NO: 14;
   (c) a nucleotide sequence that hybridizes to the complement of the nucleotide sequence of either (a) or (b) at 50° C. in a hybridization buffer comprising 0.015 M sodium chloride and 0.0015 M sodium citrate; or
   (d) a nucleotide sequence that is complementary to the nucleotide sequence of any of (a)-(c).

2. An isolated nucleic acid molecule comprising:
   (a) a region of the nucleotide sequence of any of SEQ ID NO: 1, SEQ ID NO: 3, or SEQ ID NO: 5 encoding a polypeptide of at least 25 amino acid residues;
   (b) a region of the nucleotide sequence of any of SEQ ID NO: 1, SEQ ID NO: 3, or SEQ ID NO: 5 comprising at least 16 nucleotides;
   (c) a nucleotide sequence that hybridizes to the complement of the nucleotide sequence of either (a) or (b) at 50° C. in a hybridization buffer comprising 0.015 M sodium chloride and 0.0015 M sodium citrate; or
   (d) a nucleotide sequence that is complementary to the nucleotide sequence of any of (a)-(c).

3. An isolated nucleic acid molecule comprising:
   (a) a nucleotide sequence encoding a polypeptide as set forth in any of SEQ ID NO: 2, SEQ ID NO: 4, SEQ ID NO: 6, SEQ ID NO: 7, or SEQ ID NO: 14 that has a C- and/or N-terminal truncation, wherein the encoded polypeptide is capable of specifically binding TALL-1;
   (b) a nucleotide sequence that hybridizes to the complement of the nucleotide sequence of at 50° C. in a hybridization buffer comprising 0.015 M sodium chloride and 0.0015 M sodium citrate; or
   (c) a nucleotide sequence that is complementary to the nucleotide sequence of either (a) or (b).

4. An isolated nucleic acid molecule comprising:
   (a) a region of the nucleotide sequence of any of SEQ ID NO: 1, SEQ ID NO: 3, or SEQ ID NO: 5, encoding a polypeptide comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7;
   (b) a region of the nucleotide sequence of either SEQ ID NO: 1 or SEQ ID NO: 3, encoding a polypeptide comprising amino acid residues 1-84 of the amino acid sequence as set forth in any of SEQ ID NO: 2, SEQ ID NO: 4, or SEQ ID NO: 7; or
   (c) a region of the nucleotide sequence of SEQ ID NO: 5, encoding a polypeptide comprising amino acid residues 1-83 of the amino acid sequence as set forth in SEQ ID NO: 6.

5. A vector comprising the nucleic acid molecule of any of claims 1, 2, 3, or 4.

6. A host cell comprising the vector of claim 5.

7. The host cell of claim 6 that is a eukaryotic cell.

8. The host cell of claim 6 that is a prokaryotic cell.

9. A composition comprising a nucleic acid molecule of any of claims 1, 2, 3, or 4 and a pharmaceutically acceptable formulation agent.

10. The composition of claim 9, wherein the nucleic acid molecule is comprised within a viral vector.

11. A viral vector comprising a nucleic acid molecule of any of claims 1, 2, 3, or 4.

12. A nucleic acid molecule of any of claims 1, 2, 3, or 4 attached to a solid support.

13. An array of nucleic acid molecules comprising at least one nucleic acid molecule of any of claims 1, 2, 3, or 4.

14. A process of producing a polypeptide encoded by a nucleic acid molecule having:
   (a) the nucleotide sequence as set forth in any of SEQ ID NO: 1, SEQ ID NO: 3, or SEQ ID NO: 5;
   (b) a region of the nucleotide sequence of any of SEQ ID NO: 1, SEQ ID NO: 3, or SEQ ID NO: 5 encoding a polypeptide of at least 25 amino acid residues;
   (c) a nucleotide sequence encoding a polypeptide as set forth in any of SEQ ID NO: 2, SEQ ID NO: 4, SEQ ID NO: 6, SEQ ID NO: 7, or SEQ ID NO: 14 that has a C- and/or N-terminal truncation, wherein the encoded polypeptide is capable of specifically binding TALL-1;
   (d) a region of the nucleotide sequence of any of SEQ ID NO: 1, SEQ ID NO: 3, or SEQ ID NO: 5, encoding a polypeptide comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7;
   (e) a region of the nucleotide sequence of either SEQ ID NO: 1 or SEQ ID NO: 3, encoding a polypeptide comprising amino acid residues 1-84 of the amino acid sequence as set forth in any of SEQ ID NO: 2, SEQ ID NO: 4, or SEQ ID NO: 7;
   (f) a region of the nucleotide sequence of SEQ ID NO: 5, encoding a polypeptide comprising amino acid residues 1-83 of the amino acid sequence as set forth in SEQ ID NO: 6;
   (g) a nucleotide sequence that is a degenerate variant of the nucleotide sequence of any of (a), (b), (d), (e), or (f); or
   (h) a nucleotide sequence that hybridizes to the complement of the nucleotide sequence of any of (a)-(f) at 65° C. in a hybridization buffer comprising 0.015 M sodium chloride and 0.0015 M sodium citrate;

comprising culturing a host cell containing the nucleic acid molecule under suitable conditions to express the polypeptide, and optionally isolating the polypeptide from the culture.

15. The process of claim 14, wherein the nucleic acid molecule comprises promoter DNA other than promoter DNA for a naturally occurring nucleic acid molecule encoding TALL-1R polypeptide operatively linked to the nucleic acid molecule.

16. A fusion polypeptide comprising a first polypeptide and a second polypeptide, wherein the first polypeptide is encoded by a nucleic acid molecule having:
   (a) the nucleotide sequence as set forth in any of SEQ ID NO: 1, SEQ ID NO: 3, or SEQ ID NO: 5;

(b) a region of the nucleotide sequence of any of SEQ ID NO: 1, SEQ ID NO: 3, or SEQ ID NO: 5 encoding a polypeptide of at least 25 amino acid residues;

(c) a nucleotide sequence encoding a polypeptide as set forth in any of SEQ ID NO: 2, SEQ ID NO: 4, SEQ ID NO: 6, SEQ ID NO: 7, or SEQ ID NO: 14 that has a C- and/or N-terminal truncation, wherein the encoded polypeptide is capable of specifically binding TALL-1;

(d) a region of the nucleotide sequence of any of SEQ ID NO: 1, SEQ ID NO: 3, or SEQ ID NO: 5, encoding a polypeptide comprising amino acid residues 1-40, 1-38, 11-38, or 17-38 of the amino acid sequence as set forth in any of SEQ ID NO: 2, SEQ ID NO: 4, SEQ ID NO: 6, or SEQ ID NO: 7;

(e) a region of the nucleotide sequence of either SEQ ID NO: 1 or SEQ ID NO: 3, encoding a polypeptide comprising amino acid residues 1-84 of the amino acid sequence as set forth in any of SEQ ID NO: 2, SEQ ID NO: 4, or SEQ ID NO: 7;

(f) a region of the nucleotide sequence of SEQ ID NO: 5, encoding a polypeptide comprising amino acid residues 1-83 of the amino acid sequence as set forth in SEQ ID NO: 6;

(g) a nucleotide sequence that is a degenerate variant of the nucleotide sequence of any of (a), (b), (d), (e), or (f); or (h) a nucleotide sequence that hybridizes to the complement of the nucleotide sequence of any of (a)-(f) at 65° C. in a hybridization buffer comprising 0.015 M sodium chloride and 0.0015 M sodium citrate;

and the second polypeptide has an amino acid sequence that is heterologous to the first polypeptide.

17. The fusion polypeptide of claim 16, wherein the second polypeptide is an IgG constant domain or fragment thereof.

18. The fusion polypeptide of claim 16, wherein the second polypeptide is a FLAG epitope.

19. The fusion polypeptide of claims 16, wherein the second polypeptide is fused to the N-terminus of the first polypeptide.

20. The fusion polypeptide of claim 16, wherein the second polypeptide is fused to the C-terminus of the first polypeptide.

* * * * *